United States Patent
Laser et al.

(10) Patent No.: US 11,712,245 B2
(45) Date of Patent: Aug. 1, 2023

(54) ACCELERATED PATENCY MAGNAMOSIS

(71) Applicant: MYKA LABS, INC., San Francisco, CA (US)

(72) Inventors: Daniel J. Laser, San Francisco, CA (US); John H. Jerman, Palo Alto, CA (US); Lee Swanstrom, Portland, OR (US)

(73) Assignee: MYKA LABS, INC., San Francisco, CA (US)

( * ) Notice: Subject to any disclaimer, the term of this patent is extended or adjusted under 35 U.S.C. 154(b) by 0 days.

(21) Appl. No.: 17/531,360

(22) Filed: Nov. 19, 2021

(65) Prior Publication Data

US 2022/0117603 A1   Apr. 21, 2022

Related U.S. Application Data

(63) Continuation of application No. PCT/US2021/055650, filed on Oct. 19, 2021.
(Continued)

(51) Int. Cl.
*A61B 18/14* (2006.01)
*A61B 17/11* (2006.01)
(Continued)

(52) U.S. Cl.
CPC ........ *A61B 17/1114* (2013.01); *A61B 18/082* (2013.01); *A61B 18/20* (2013.01);
(Continued)

(58) Field of Classification Search
CPC ... A61B 18/082; A61B 18/20; A61B 18/1442; A61B 2018/00494; A61B 2018/00595;
(Continued)

(56) References Cited

U.S. PATENT DOCUMENTS 5,328,488 A * 7/1994 Daikuzono ............ A61B 18/22
606/17
5,330,486 A * 7/1994 Wilk .................... A61B 17/115
227/181.1
(Continued)

FOREIGN PATENT DOCUMENTS

DE    102016013422    9/2017
WO    2014102621    7/2014
(Continued)

OTHER PUBLICATIONS

Foster et al., "A chitosan based, laser activated thin film surgical adhesive, 'SurgiLux': preparation and demonstration," J Vis Exp. Oct. 23, 2012;(68):3527 (abstract only).
(Continued)

*Primary Examiner* — Thomas A Giuliani
(74) *Attorney, Agent, or Firm* — FisherBroyles LLP; John Shimmick

(57) ABSTRACT

A system is configured to bring about anastomosis between two lumens in a patient or between two sections of a single lumen in a patient. The anastomosis system includes a first tissue-compressing element, a second tissue-compressing element, and an energy source. The energy source can be a thermal energy source or laser energy source. Tissue is interposed between the elements. Magnetic material incorporated into the tissue-compressing elements facilitates the alignment of the elements as well as compression of the interposed tissue. The energy source can deliver energy to tissue. This delivery of energy can cause local changes to the tissue that can help maintain positional stability of the implants, can bring about immediate patency of the anastomosis and can otherwise facilitate achieving desired outcomes for the patient.

19 Claims, 21 Drawing Sheets

Related U.S. Application Data

(60) Provisional application No. 63/198,465, filed on Oct. 20, 2020.

(51) Int. Cl.
*A61B 18/08* (2006.01)
*A61B 18/20* (2006.01)
*A61B 17/00* (2006.01)
*A61B 18/00* (2006.01)

(52) U.S. Cl.
CPC ............ *A61B 2017/00876* (2013.01); *A61B 2018/00494* (2013.01); *A61B 2018/00595* (2013.01)

(58) Field of Classification Search
CPC .. A61B 2018/00607; A61B 2018/0063; A61B 2018/00619; A61B 17/1114; A61B 17/11; A61B 17/115; A61B 2017/00876; A61B 2017/1125
USPC ....... 606/41, 45, 48–52, 2, 139, 151, 153, 8, 606/219
See application file for complete search history.

(56) References Cited

U.S. PATENT DOCUMENTS

| | | | |
|---|---|---|---|
| 5,441,507 A | 8/1995 | Wilk | |
| 5,830,224 A * | 11/1998 | Cohn | A61B 17/11 606/167 |
| 6,059,781 A | 5/2000 | Yamanashi | |
| 6,391,049 B1 * | 5/2002 | McNally | A61L 31/148 606/214 |
| 6,458,141 B1 * | 10/2002 | Peyman | A61F 9/008 606/166 |
| 6,699,240 B2 | 3/2004 | Francischelli | |
| 6,802,847 B1 | 10/2004 | Carson | |
| 8,142,454 B2 | 3/2012 | Harrison | |
| 8,623,036 B2 | 1/2014 | Harrison | |
| 8,870,899 B2 | 10/2014 | Beisel | |
| 10,285,702 B2 | 5/2019 | Jose | |
| 10,463,293 B2 | 11/2019 | Maharbiz | |
| 10,568,630 B2 | 2/2020 | Hernandez | |
| 10,667,817 B2 | 6/2020 | Gagner et al. | |
| 10,682,143 B2 | 6/2020 | Hernandez | |
| 10,722,292 B2 | 7/2020 | Arya | |
| 2004/0120668 A1 | 6/2004 | Loeb | |
| 2005/0192603 A1 | 9/2005 | Cole | |
| 2006/0111698 A1 | 5/2006 | Kwon | |
| 2008/0114384 A1 | 5/2008 | Chang | |
| 2012/0265183 A1 * | 10/2012 | Tulleken | A61B 18/24 606/10 |
| 2013/0253548 A1 | 9/2013 | Harrison | |
| 2014/0163664 A1 | 6/2014 | Goldsmith | |
| 2015/0164508 A1 | 6/2015 | Hernandez | |
| 2015/0342608 A1 | 12/2015 | Hernandez | |
| 2016/0095599 A1 | 4/2016 | Jose | |
| 2017/0156658 A1 | 6/2017 | Maharbiz | |
| 2017/0265866 A1 * | 9/2017 | Ryou | A61B 17/3478 |
| 2019/0247050 A1 | 8/2019 | Goldsmith | |
| 2020/0138438 A1 | 5/2020 | Harrison | |
| 2020/0187947 A1 | 6/2020 | Hernandez | |
| 2021/0007744 A1 | 1/2021 | Hernandez | |
| 2021/0145445 A9 | 5/2021 | Goldsmith | |

FOREIGN PATENT DOCUMENTS

| | | |
|---|---|---|
| WO | 2014176458 | 10/2014 |
| WO | 2015195720 | 12/2015 |
| WO | 2019006194 | 1/2019 |

OTHER PUBLICATIONS

Hatayama, Hitoshi, et al., "Study on Use of Blue-violet Laser Diode Module as Dental/Oral Surgical Device," SEI Technical Review, 66:142-146 (Apr. 2008).

International Search Report and Written Opinion for PCT/US2021/055650, 18 pages (dated Mar. 1, 2022).

* cited by examiner

ACCELERATED PATENCY MAGNAMOSIS

RELATED APPLICATIONS

This application is a bypass continuation of International Patent Application No. PCT/US2021/055650, filed Oct. 19, 2021, which claims the benefit under 35 U.S.C. § 119(e) of U.S. Provisional Patent Application No. 63/198,465, filed Oct. 20, 2020, and titled "ACCELERATED PATENCY MAGNAMOSIS," which are incorporated, in their entirety, by this reference.

BACKGROUND

Embodiments of the present disclosure are directed toward systems, devices, compositions, and methods for modifying anatomy. More particularly, the present disclosure is directed toward systems, devices, compositions, and methods for creating an anastomosis or otherwise similarly joining anatomical elements with lumens, such as two sections of the bowel, such modification being intended to achieve therapeutic effects such as correcting a congenital malformation, repairing an injury, or treating a disorder affecting or involving the gastrointestinal tract.

In caring for patients with a variety of medical conditions, care providers can have reason to create an anastomosis in the bowel. For example, traumatic injury affecting the bowel can necessitate removal of a section of the bowel, such that, upon removal of an injured section of the bowel, restoration of bowel function can be accomplished by surgically connecting the remaining proximal and distal portions of the bowel to one another, such that food and digestive juices can pass from the stomach to the large intestine while undergoing small bowel digestive processes.

In treating colorectal cancer, surgical removal of a section of the large bowel is routinely carried out. As in the example of small bowel procedures, restoration of large bowel function can be accomplished by surgically connecting the remaining proximal and distal sections of the large bowel to one another. However, prior approaches to surgically connecting remaining portions of bowel can be less precise than would be ideal in at least some instances.

A connection created between two lumens such as two section of the small bowel is commonly referred to as anastomosis. Anastomosis creation can be carried out by hand-sewing, by stapling, and by non-stapling methods involving compression, such as by interposing tissue to be anastomosed between components of a multi-component device where the components incorporate magnetic elements.

For devices designed to bring about anastomosis over time using compression, there can be a tendency for an anastomosis device to become repositioned subsequent to its initial positioning by a surgeon. For example, patient movement can result in repositioning. Such repositioning can be deleterious in at least some instances. For example, repositioning can slow a healing process. Suturing can be used to maintain locational stability of a compression-based anastomosis device. However, access for suturing can increase the level of invasiveness of a procedure. For example, for an anastomosis procedure where positioning of the device is accomplished with a single laparoscopic port, suturing can require a second port in at least some instances.

When a surgical intervention is carried out on a patient that includes anastomosis creation in the bowel, it may be preferred for such an anastomosis in the bowel to have the capacity to pass food or digestive waste shortly after surgical intervention. Capacity to pass food or digestive waste is often referred to as patency. For a compressive anastomosis, patency of the anastomosis can be achieved through necrosis of compressed tissue. Such necrosis can occur over a period of several days.

Although compressive anastomosis can be effective, work in relation to the present disclosure suggests that it would be helpful to form the anastomosis more quickly in at least some instances. A knife apparatus can be used to achieve immediate patency. However, knife firing mechanisms can be complex and may be susceptible to misfiring or other failure modes, with the knife failing to completely cut the tissue or becoming jammed and posing a potential risk to the patient. Also, prior approaches to cutting tissue can be less accurate than would be ideal in at least some instances.

In light of the above, there is a need for systems, devices, methods and apparatus that ameliorate at least some of the aforementioned limitations of the prior approaches.

SUMMARY

In some embodiments, the presently disclosed methods, systems, devices and apparatus promote a healthy anastomosis where the positional stability of an anastomosis device is maintained after initial placement and with patency soon after a surgeon positions an anastomosis device.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

The present application is further understood when read in conjunction with the appended drawings. For the purpose of illustrating the subject matter, there are shown in the drawings exemplary embodiments of the subject matter. However, the presently disclosed subject matter is not limited to the specific systems, devices, compositions, and methods disclosed. In addition, the drawings are not necessarily drawn to scale. In the drawings.

DETAILED DESCRIPTION

Figure 1:
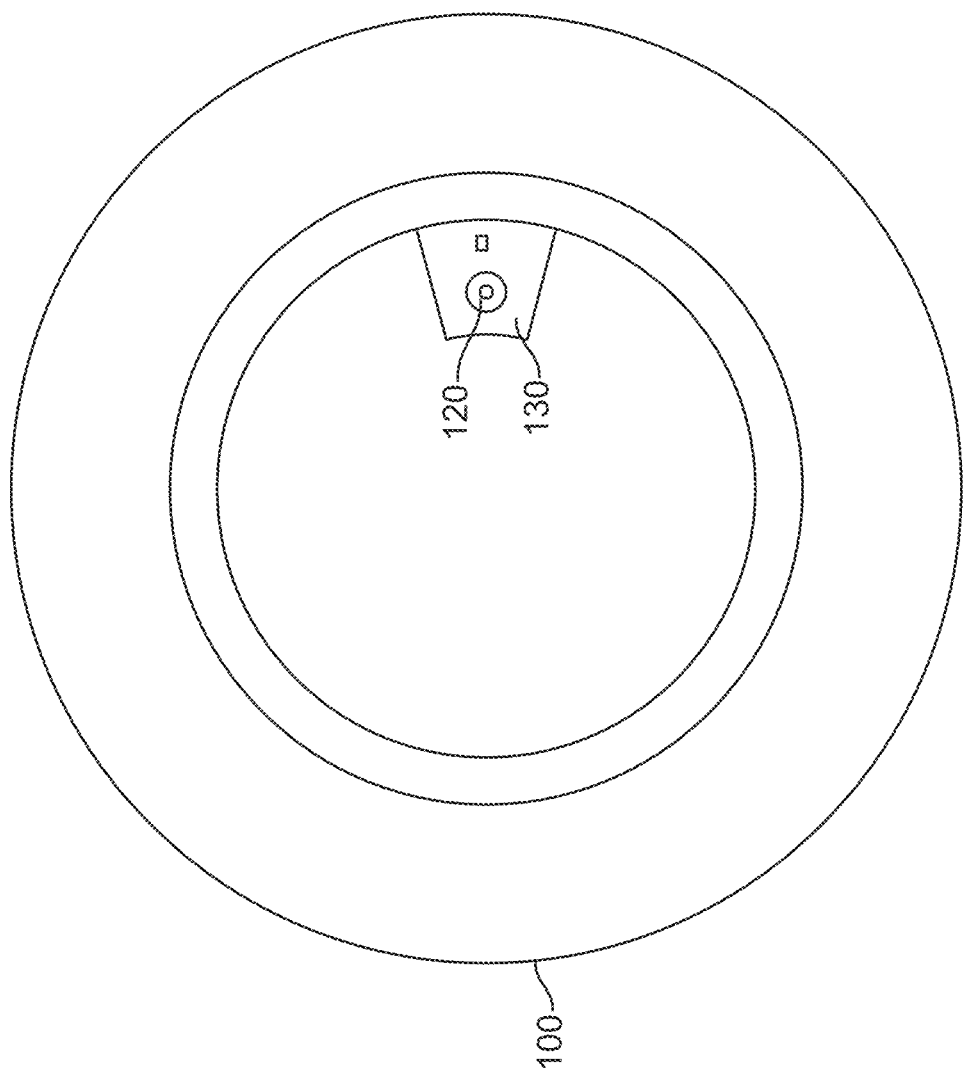
FIG. 1 shows a compressive element of an anastomosis system with a laser energy source, in accordance with some embodiments.

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Some embodiments of the present disclosure relate generally to anastomosis devices that combine, firstly, a plurality of magnetic element-inclusive components to compress interposed layers of tissue and, secondly, thermal energy and laser light sources for physically altering regions of interposed tissue, or regions of tissue in close proximity to regions of interposed tissue, to facilitate therapeutic effects, such as changing the properties of tissue.

The presently disclosed methods, systems and apparatus are well suited for combination prior approaches to forming an anastomosis and may comprise one or more components of such devices. For example, systems comprising tissue-compressing elements with one element having a concave face and a second element having a convex face are described in U.S. Pat. No. 8,142,454, the entire disclosure of which is incorporated herein by reference. The presently disclosed systems and methods are well suited for combination with one or more components of a surgical robotics system, such as the da Vinci surgical system, commercially available from Intuitive Surgical. In some embodiments, one or more system components can be placed with a surgical robotics system, such as single port access, for example as can be performed with the da Vinci SP surgical system, commercially available from Intuitive Surgical.

In some embodiments, an anastomosis device comprises a plurality of tissue-compressing elements and a thermal energy source. The configuration of the plurality of tissue-compressing elements is such that layers of tissue can be interposed between tissue-compressing elements. In some embodiments, said anastomosis device comprises two elements each comprising at least one an approximately toroidal magnetic element and having an approximately annular face. Upon mating said at least two elements with an interposing region of multi-layer tissue contacted on one side by an annular face of a first component and on an opposing side by an annular face of a second component, said interposing multi-layer tissue can be compressed as a result of the magnetic force exerted between the at least two device components. In some embodiments, the thermal energy source comprises an approximately annular resistive heating element integrated in an assembly with a tissue-compressing element and concentrically positioned within said assembly relative to said tissue-compressing element. In some embodiments, power to said heating element is sourced from a power supply located outside the patient's body by a wired connection. In some embodiments, power to said heating element is sourced from a battery integrated in an assembly with said heating element. In some embodiments, power to said heating element is wirelessly transmitted from a power supply.

In some embodiments, an anastomosis device comprises a plurality of tissue-compressing elements and a laser energy source. The configuration of the plurality of tissue-compressing elements is such that layers of tissue can be interposed between tissue-compressing elements. In some embodiments, there are two components each incorporating at least one an approximately toroidal magnetic element and having faces that are approximately annular. Upon mating said at least two elements with an interposing region of multi-layer tissue contacted on one side by an annular face of a first component and on an opposing side by an annular face of a second component, said interposing multi-layer tissue is compressed as a result of the magnetic force exerted between the at least two device components.

In some embodiments, the laser energy source is configured to apply laser energy to said interposing multi-layer tissue regions, or multi-layer tissue regions in close physical proximity to the interposed multi-layer tissue regions. In some embodiments, the laser energy source can apply laser energy to a region of said interposing multilayer tissue that is centrally located related to the inner diameter of a tissue-contacting face of an approximately annular magnetic component. Such application of laser energy can produce anatomical changes in said tissue that can enhance the positional stability of mated components or otherwise contribute to formation of a healthy anastomosis. For example, a change in the rheological properties of said tissue can enhance the positional stability of mated components. As another example, a swelling effect in said tissue can enhance the positional stability of mated components. As another example, a cauterizing effect on said tissue by such application of laser energy can promote healing. As another example, tissue-fusing effects of such application of laser energy can promote a leak-free anastomosis.

In some embodiments, the laser energy source can translate through space. For example, the laser energy source can translate along a circular pathway. Translation of the laser energy source along a circular pathway can be facilitated by a circular track structure that is part of the disclosure. The track structure can be mounted on or integrally part of a tissue-compressing element of the disclosure. The laser energy source can be affixed within a holder that is mechanically interfaced with the track structure such that the holder can move along the circular path while motion of the holder in other directions is constrained or prevented.

In some embodiments, translation of the laser energy source through space can be driven by a motor. In some embodiments, the motor can operate autonomously for periods of time. In some embodiments, operation of the motor can be controlled by input from a user.

In some embodiments, the laser energy source comprises a visible or infrared laser. The power emitted by a visible or infrared laser can be between five and 20 watts. The laser energy can be coupled to the aperture by a fiber. The fiber can be bendable and twistable such that translation of the aperture on a circular path can occur without damage to the fiber. The laser can be produced by a source that remains outside the patient during the procedure. In certain embodiments, the laser light may be pulsed with pulse widths between 1 picosecond and 100 nanoseconds.

In some embodiments, the laser energy source comprises a laser diode that is coupled to a tissue-compressing element and that can be operated inside a patient. In some embodiments, the laser diode can be positioned centrally relative to an approximately annular tissue-compressing element, optionally with the structure holding the laser diode having openings to allow material to flow through the annulus, for example while an anastomosis is healing. In some embodiments, the laser diode can translate through space. In some embodiments, the laser diode can translate on a circular pathway. In some embodiments, the laser diode and its power systems and controller components can be co-located with the laser diode. In some embodiments, power to operate the laser diode can be provided by a power module that can be positioned near to said laser energy means but outside the lumen, with power transferred inductively. Said power module can be positioned laparoscopically.

In some embodiments, the system further comprises a means for capturing stray light. The stray light capturing means can be a material that absorbs light at the wavelengths used. The light absorbing material can be configured into a disk, annular or toroidal shape and attached to the second compressing element opposite the positions that the laser energy source can translate through as constrained by a circular track.

In some embodiments, a system comprises tissue-compressing elements, a light energy source and a material that changes properties upon exposure to light. The material can be a photopolymerizable polymer that, upon photopolymerization, can cause a tissue-compressing element to adhere to tissue. The photopolymerizable material can facilitate fusing of tissue layers to facilitate creation of a leak-free anastomosis. In another embodiment, a thermally activated material can be used, where laser light energy can increase the temperature of thermally activated material to bring about adherence effects or tissue-fusing effects.

In some embodiments, each tissue-compressing element comprises a plurality of magnetic elements. For example, each of two tissue-compressing elements can comprise three magnetic elements, such that upon mating said two tissue-compressing elements, said magnets provide both axial alignment effects, as with a single toroidal magnet, as well as constraining said tissue-compressing elements from rotating relative to one another. Physical features of tissue-compressing elements can also kinematically constrain tissue-compressing elements upon mating with interposed tissue.

In some embodiments, surface roughness or features such as bumps or ridges can facilitate positional stability of tissue-compressing elements upon mating with interposed tissue.

In some embodiments, the device disclosed herein can create an anastomosis in the large bowel. In some embodiments, the device disclosed herein can create an anastomosis in the small bowel. In some embodiments, the device disclosed herein can create an anastomosis between the small bowel and the stomach.

In some embodiments, the disclosure provides a method for creating an anastomosis within a portion of a patient's body. The method includes locating an anastomosis assembly at a treatment site and mating the tissue-compressing elements of the assembly with interposing multilayer tissue and applying laser energy.

In some embodiments, the treatment site can be determined using guidance from at least one of a pre-operative diagnostic tool and a bony landmark of the patient. In additional embodiments, the treatment site can be determined without use of real-time imaging.

As described herein, a "magnamosis" is an anastomosis that is created through compression of a multilayer tissue region by a plurality of elements incorporating magnetic materials.

In some embodiments, compression of the interposing multilayer tissue can be described by a pressure gradient with higher pressures applied to more central regions of interposed multilayer tissue and lower pressures applied to more peripheral regions of interposed multilayer tissue.

Systems, devices, compositions, and methods for creating an anastomosis within a patient's body are described herein. The methods include locating a plurality of components in a plurality of lumens within the patient's body or at a plurality of positions within a single lumen, bringing the components into proximity so that they can mate, and applying laser energy to tissue. In some embodiments, this laser energy is capable of improving the magnamosis by providing improved positional stability of the tissue-compressing elements during anastomosis formation.

Systems, devices, compositions, and methods for treating one or more pathologies associated with a patient's gastrointestinal tract are included in the subject disclosure. Systems according to the subject embodiments include elements for compressing tissue and laser units used in conjunction with one another to bring about anastomosis.

FIG. 1 shows a compressive element and a laser light source in accordance with an embodiment of the disclosed subject matter. As is provided in FIG. 1, a system includes a compressive element 100. A laser light source 120 is held by guide comprising a holder 130. In the embodiment depicted in FIG. 1, the compressive element 100 is approximately toroidal in shape. In alternative embodiments, the compressive element may have another shape.

Figure 2:
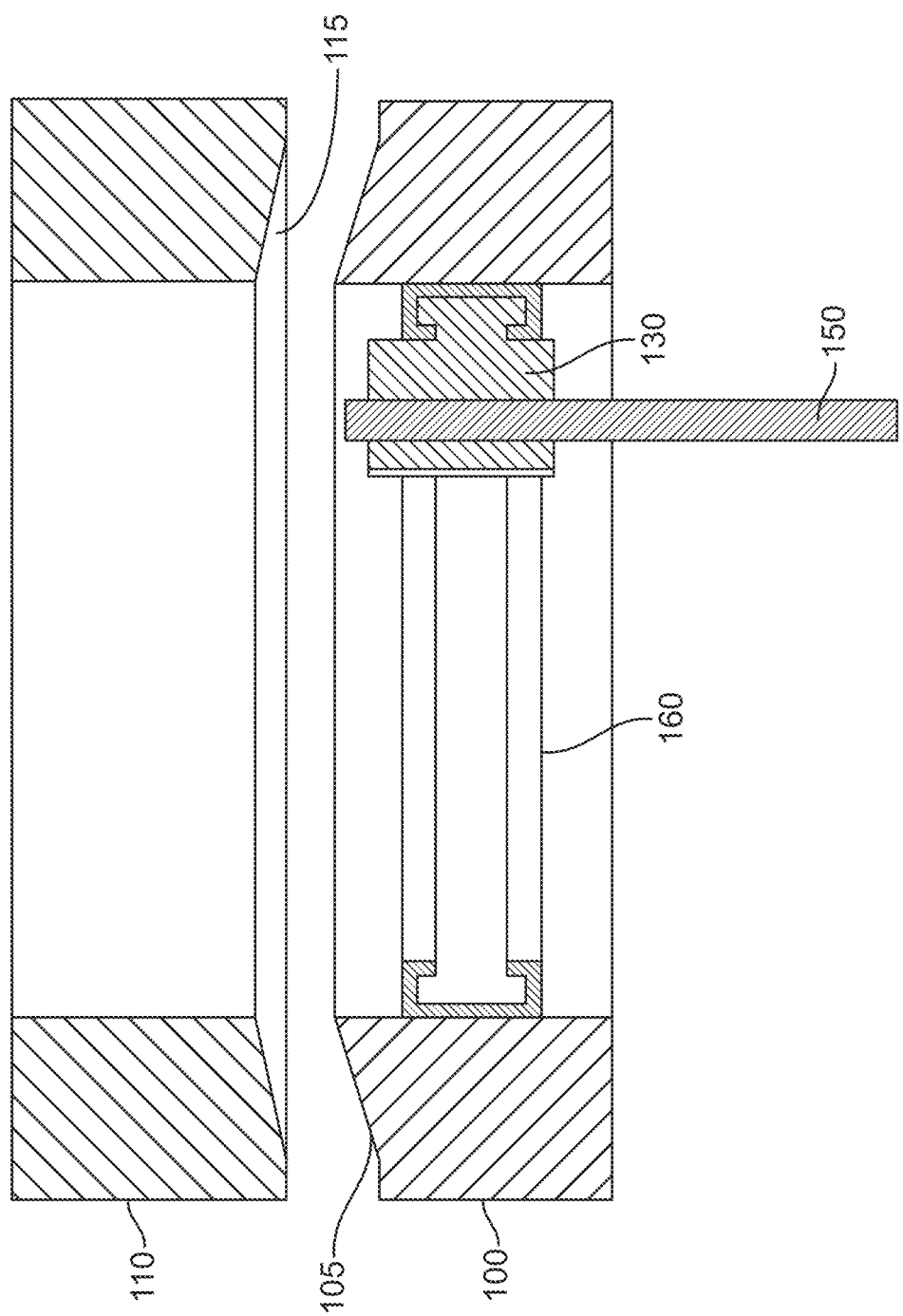
FIG. 2 shows a section illustration of an anastomosis system including a first compressive element and a second compressive element and a laser energy source, in accordance with some embodiments.

FIG. 2 shows a section illustration of a pair of compressive elements and a laser light source. As shown in FIG. 2, the first compressive element 100 has a tissue-contacting face 110. A second compressive element 105 has a tissue-contacting face 115. In some embodiments, for compressive elements comprising approximately toroidal magnetic elements, the first compressive element and second compressive element are axially self-aligning. A laser light delivery means 150 is oriented such that laser light can be directed onto a surface of tissue that can be interposed between tissue-contacting faces of compressive elements. The laser light delivery means 150 is held by a holder 130. A race or raceway apparatus 160 is positioned within the inner curved surface of the first compressive element 100 and is configured to interface with the holder 130. The guide such as a race is configured to facilitate translation of the holder 130 and of the laser light delivery means 150 on an approximately circular trajectory while constraining translation and rotation other than said translation along an approximately circular pathway. The interface configuration depicted in FIG. 2 is one of many interface architectures that facilitate translation in a circular pathway while otherwise constraining translation and rotation as described herein.

It can be readily observed that the apparatus in FIG. 2 is conducive to applying laser energy at multiple points describing a circular or annular region of tissue corresponding to the circular pathway associated with the race 140.

Figure 3:
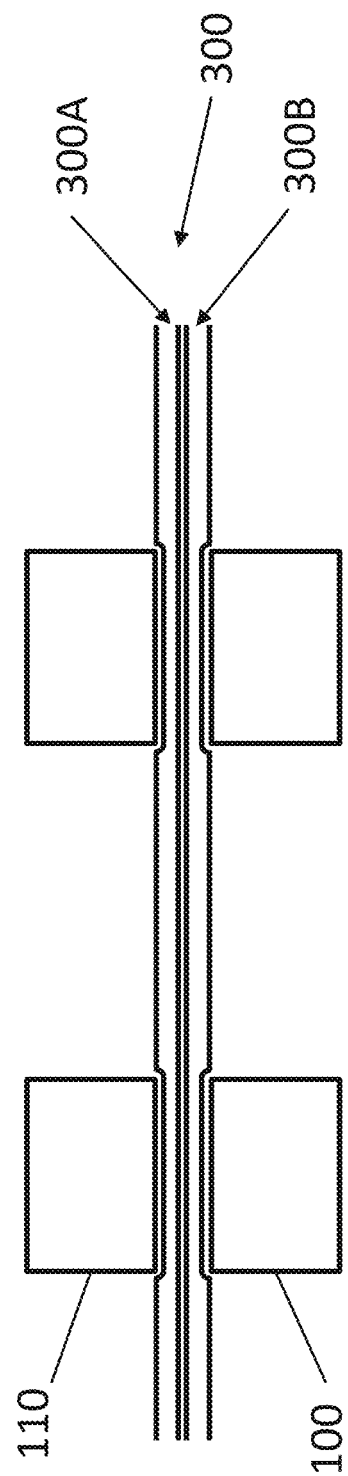
FIG. 3 is a schematic illustration of compression of interposed multilayer tissue by magnamosis device with annular tissue-compressing elements, in accordance with some embodiments.

Tissue can be compressed by a pair of elements comprising magnetic materials. FIG. 3 schematically depicts compression of a multilayer tissue region 300 by a first element 100 and a second element 105. The multilayer tissue region may comprise a first tissue section 300A, such as a first intestinal section, and a second tissue section 300B, such as a second intestinal section, which are brought into contact to form an anastomosis. Although reference is made to intestinal sections, the tissue brought into contact may comprise any suitable tissue to form an anastomosis.

Figure 4:
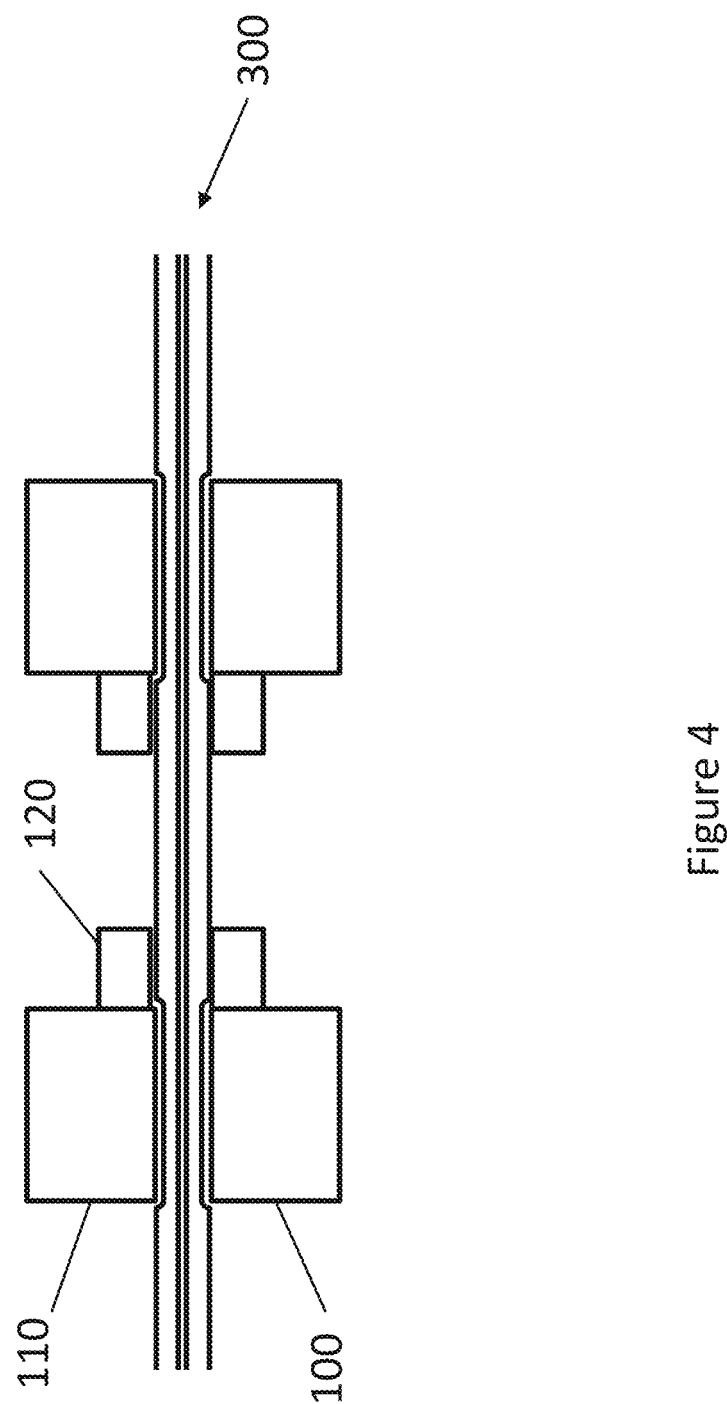
FIG. 4 is a schematic illustration of tissue-compressing elements where heating elements are integrated in assemblies with said tissue-compressing elements, in accordance with some embodiments.

Tissue can be affected by thermal energy. For example, localized heating of tissue can confer injury that is associated with swelling. Localized heating of multilayer tissue can have welding effects. FIG. 4 schematically depicts an approximately annular heating element 120 integrated in an assembly with a tissue-compressing element 110, where the heating element 120 is nested within the tissue-compressing element 110 and the heating element 120 and the tissue-compressing element 110 are approximately concentric. It can be readily observed that the heating element 120 can deliver thermal energy to a region of tissue internal to the tissue-compressing element.

Figure 5:
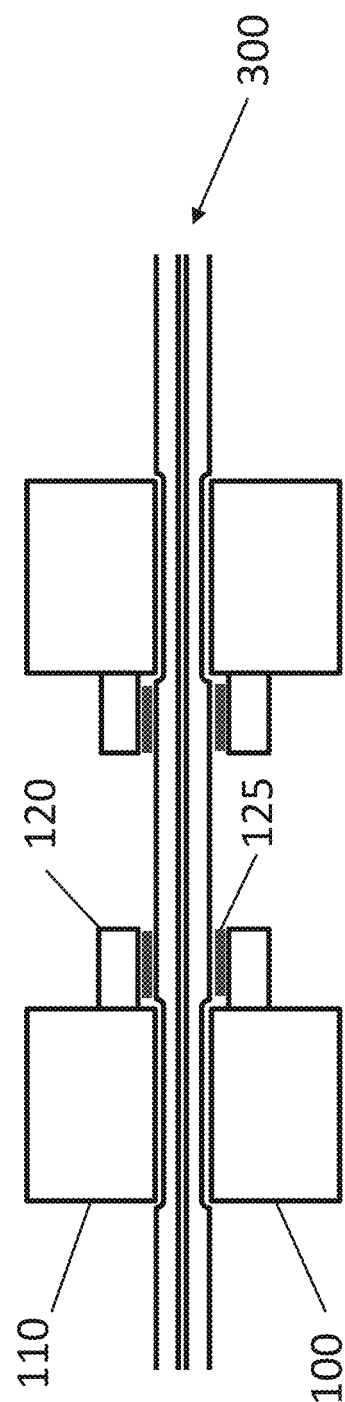
FIG. 5 is a schematic illustration of tissue-compressing elements of the intervention integrated with heating elements and with thermally activated adhesive, in accordance with some embodiments.

Thermally activated adhesives can be used in combination with heating elements and tissue-compressing elements. FIG. 5 schematically depicts an approximately annular heating element 120 integrated in an assembly with a tissue-compressing element 110, where, as in FIG. 4, the heating element 120 is nested within the tissue-compressing element 110 and the heating element 120 and the tissue-compressing element 110 are approximately concentric. Layers of adhesive 125 are affixed to tissue-contacting faces of said heating elements. Said heating elements can be used to transiently increase the temperature of said layers of adhesive above a threshold to activate adhesive functionality. Because anastomosis formation entails necrosis of the central region of bowel wall anastomosis, the constraints on maximum temperatures and other safety considerations that generally apply to heating of tissue can be less stringent than in applications entailing heating of tissue that is intended to remain viable.

Figure 6:
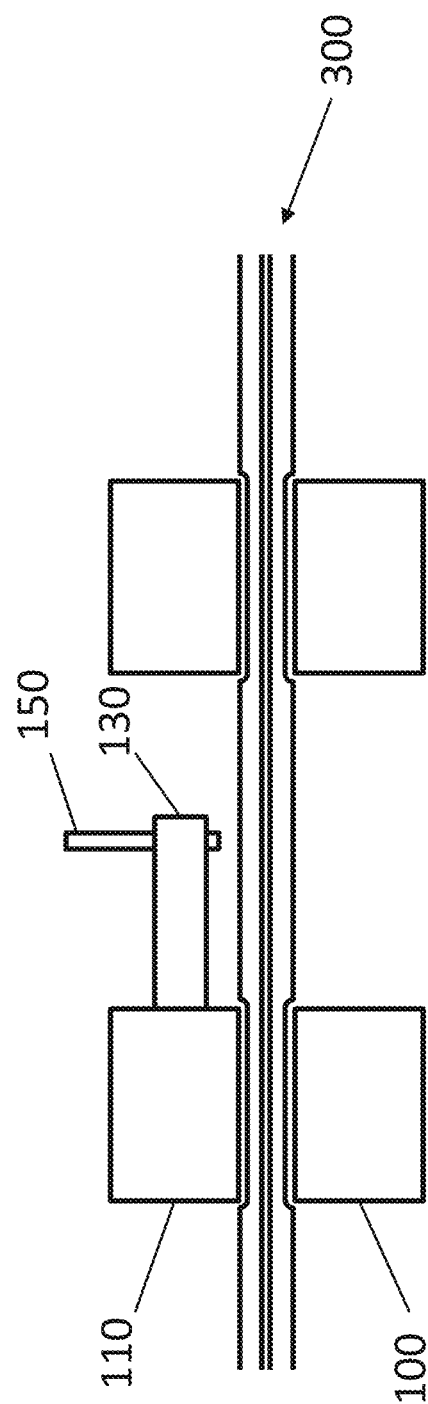
FIG. 6 is a schematic illustration of tissue-compressing elements where a laser energy delivery means and a holder are integrated in an assembly with a tissue-compressing element, in accordance with some embodiments.

Tissue can be acted on by laser energy. Laser energy can affect tissue in a variety of ways. For example, laser energy can confer injury that is associated with swelling. FIG. 6 schematically depicts a laser energy delivery means 150 integrated in an assembly with a tissue-compressing element 110, said assembly further comprising a holder 130. It can be readily observed that the laser energy delivery means 150 can deliver laser energy to a central region of tissue and that the magnitude of laser energy delivered and other parameters can be chosen to bring about desired effects in the tissue. For example, tissue can be ablated by laser injury, caused to swell up by laser energy, cauterized by laser energy, or a combination of some or all of these.

Figure 7:
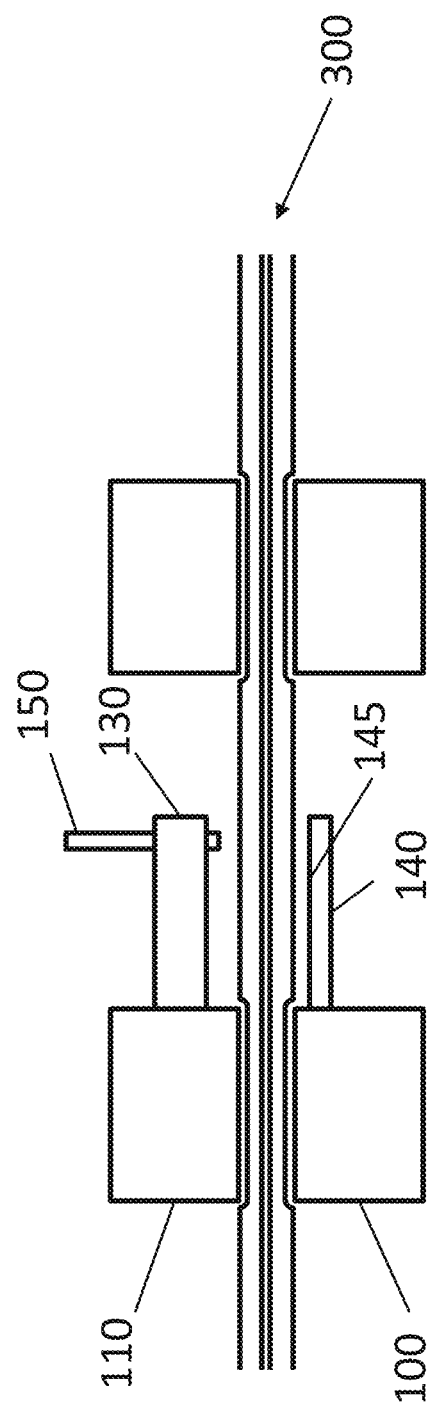
FIG. 7 is a schematic illustration of tissue-compressing elements where a laser energy delivery means and a holder are integrated in an assembly with a tissue-compressing element and where a means of capturing stray light is integrated in an assembly with a tissue-compressing element, in accordance with some embodiments.

In medical interventions involving application of laser energy, it can be advantageous to minimize exposure of non-targeted tissue to said laser energy. FIG. 7 depicts a means of capturing stray light 140 integrated with a tissue-compressing element 100. The stray light capturing means can be have a surface 145 that is highly absorptive at light wavelengths emitted by the laser energy delivery means 150.

Figure 8:
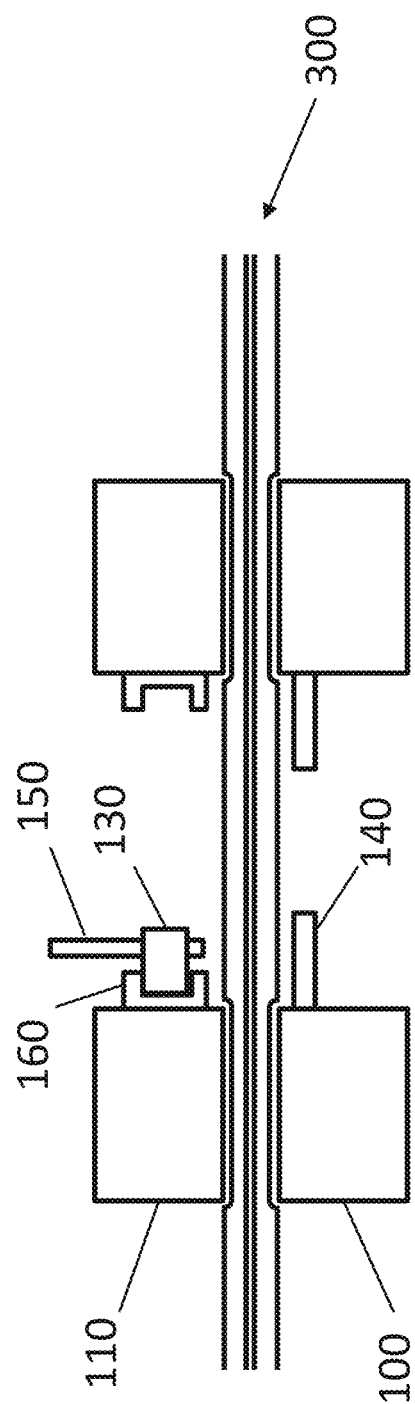
FIG. 8 is a schematic illustration of tissue-compressing elements where a race, a laser energy delivery means and a holder are integrated in an assembly with a tissue-compressing element and where said holder and laser energy source can slide in said race, in accordance with some embodiments.

Similarly to FIG. 2, FIG. 8 schematically depicts a laser energy delivery means 150 integrated in an assembly with a tissue-compressing element 110, said assembly further comprising a holder 130 and a race or raceway 160.

Figure 9:
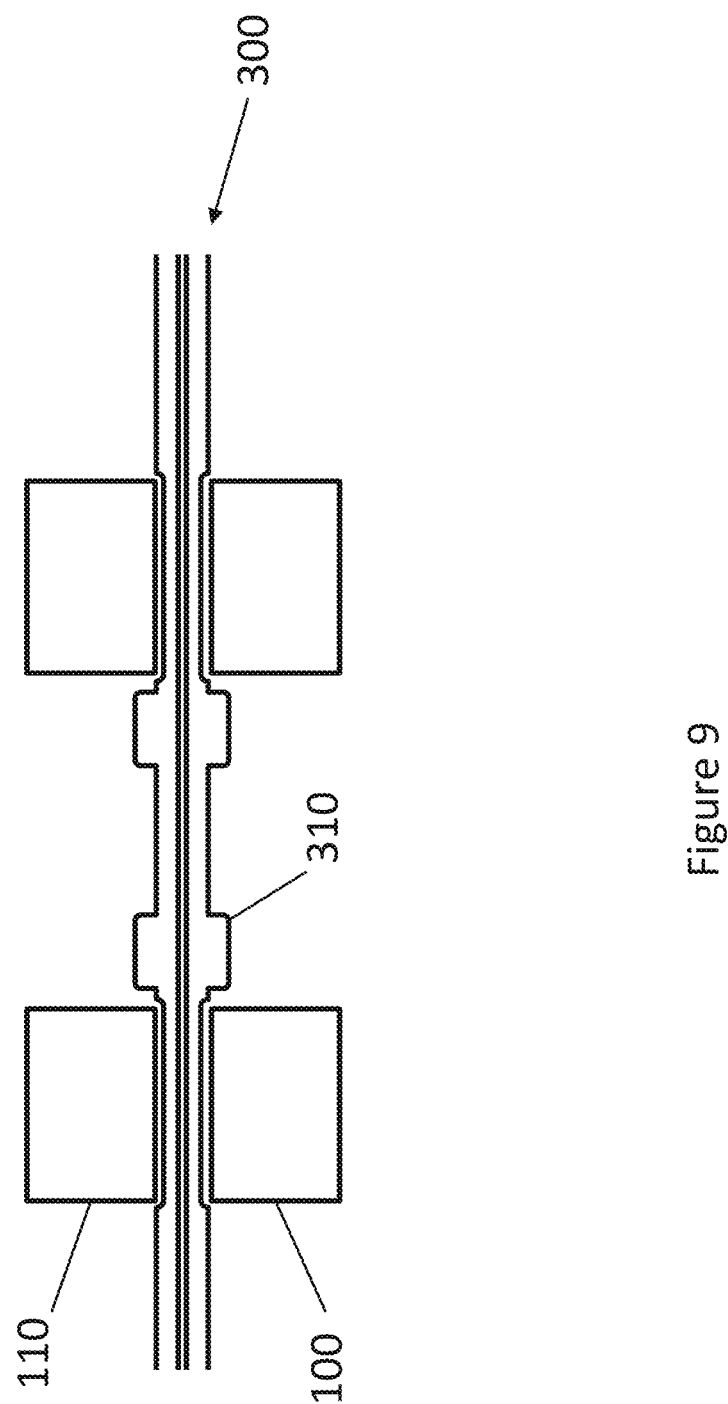
FIG. 9 is a schematic illustration of effects on interposed multilayer tissue associated with use in a patient, with localized tissue edema from application of heat or laser energy conferring enhanced positional stability on the mated compressive elements, in accordance with some embodiments.

Localized delivery of thermal energy or laser energy can be associated with localized swelling that can confer positional stability of a first tissue-compressing element 100 and second element 110 during anastomosis formation. FIG. 9 schematically depicts localized tissue swelling 310 conferring positional stability of a first element 100 and a second element 110 during anastomosis formation.

Figure 10:
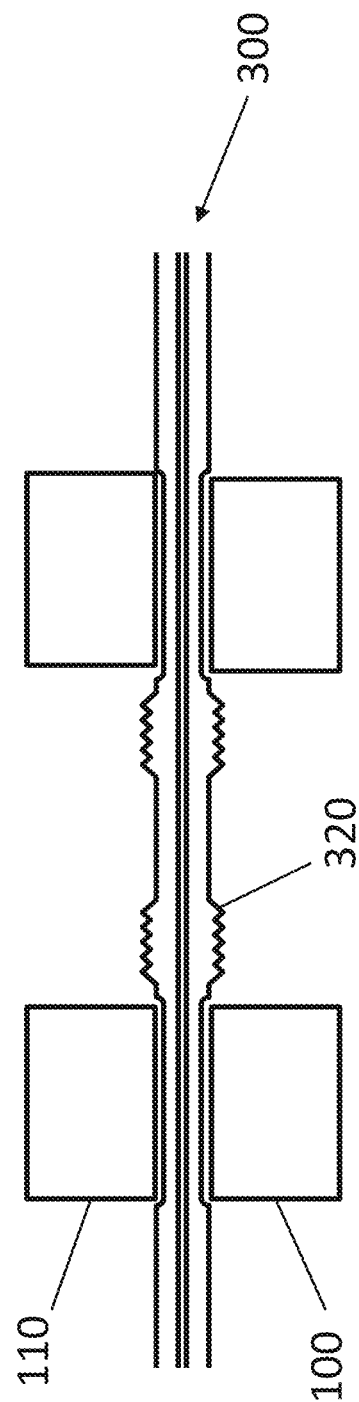
FIG. 10 is a schematic illustration of effects on interposed multilayer tissue associated with use in a patient, with localized altered tissue rheology from application of heat or laser energy conferring enhanced positional stability on the mated compressive elements, in accordance with some embodiments.

Localized delivery of thermal energy or laser energy can be associated with localized changes in rheological properties of tissue that can confer positional stability of a first tissue-compressing element 100 and second tissue-compressing element 110 during anastomosis formation. FIG. 10 schematically depicts localized changes in tissue rheological properties 320 conferring positional stability of a first element 100 and second element 110 during anastomosis formation.

Figure 11:
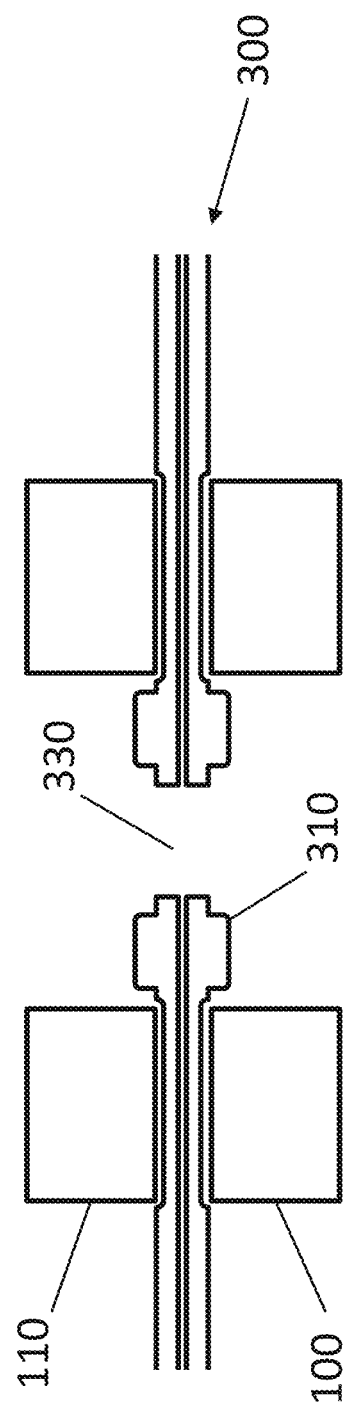
FIG. 11 is a schematic illustration of effects on interposed multilayer tissue associated with use in a patient, with localized tissue edema from application of heat or laser energy conferring enhanced positional stability on the mated compressive elements and with patency of the anastomosis brought about in whole or in part through application of laser energy by a laser energy source, in accordance with some embodiments.

Localized delivery of laser energy or thermal energy to tissue can be associated with a combination of localized ablation and other localized tissue effects. FIG. 11 schematically depicts a combination of swelling and ablation that can be brought about through application of laser energy, where said localized swelling 310 confers positional stability and said ablation confers patency 330 of the anastomosis.

Figure 12:
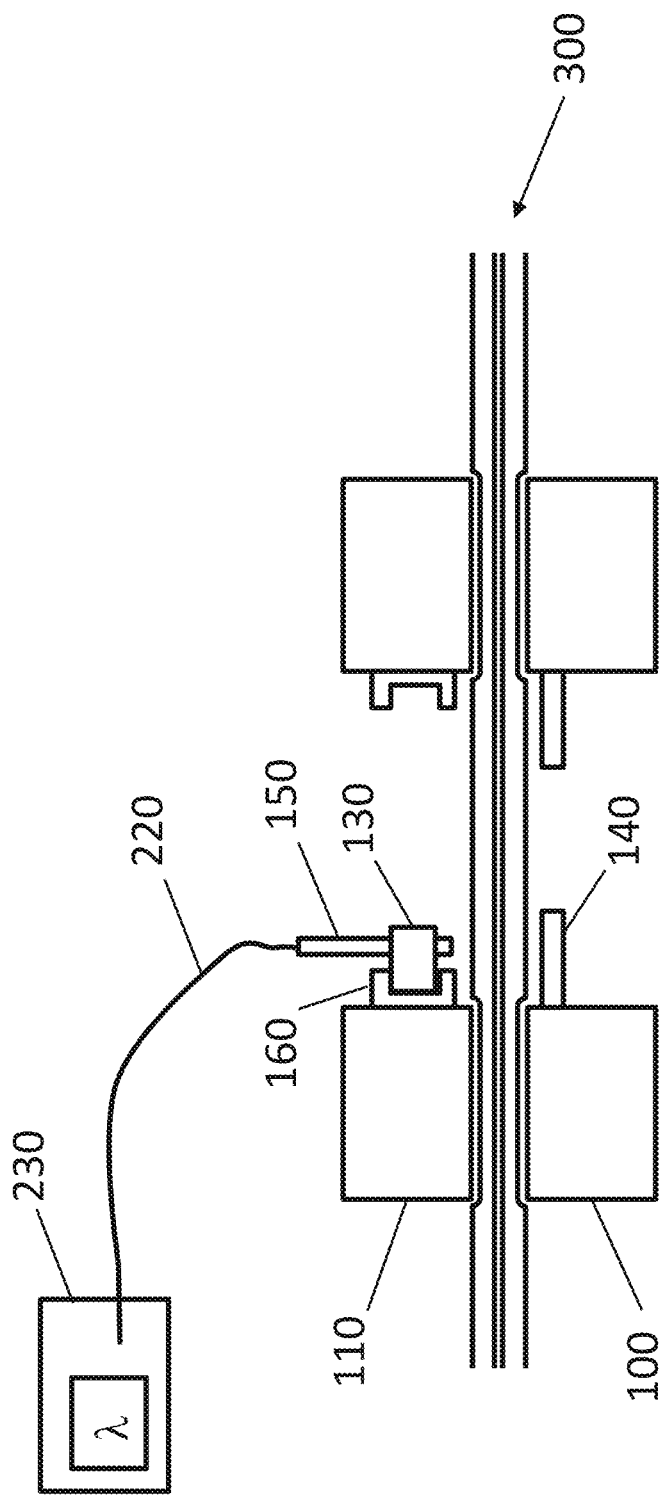
FIG. 12 is a schematic illustration of a system comprising tissue-compressing elements, a laser energy delivery means, a laser energy source and a laser fiber, in accordance with some embodiments.

A laser energy delivery means requires a source of laser energy. A wide variety of systems can produce laser energy. FIG. 12 schematically depicts a laser energy source 230 and a laser fiber 220 connecting said laser energy source to a laser energy delivery means 150. Different wavelengths can be directed down the same fiber at different times during a procedure. For example, a first wavelength can be used to bring about cauterization or welding effects in tissue. A second wavelength can be used to cut tissue.

Figure 13:
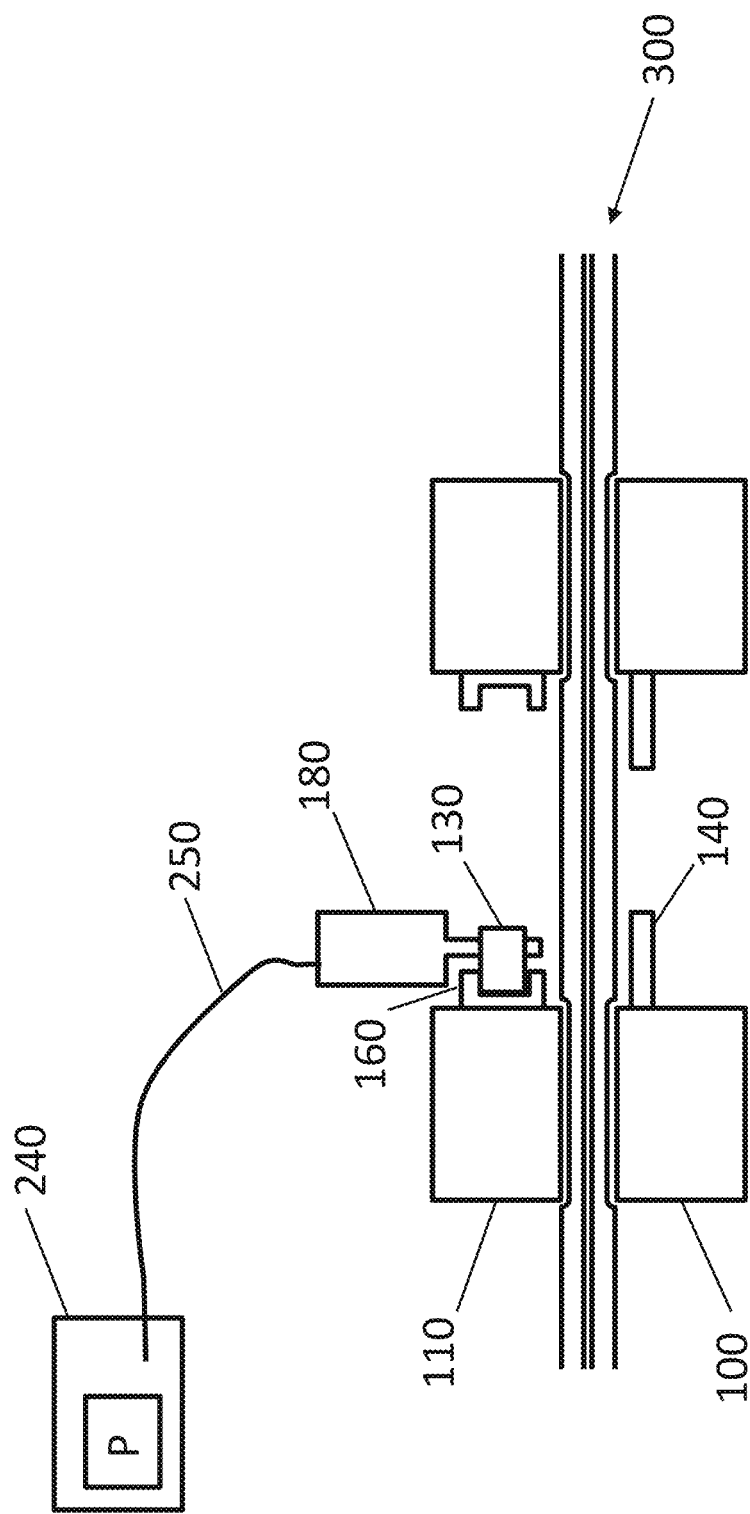
FIG. 13 is a schematic illustration of a system comprising tissue-compressing elements, a laser energy delivery means, a laser power supply and controller unit, and an interconnecting cable, in accordance with some embodiments.

A diode laser or other compact laser energy source can be integrated with a tissue-compressing element. FIG. 13 schematically depicts a compact laser energy source 180 integrated in an assembly with a tissue-compressing element 110 and a holder 130. Said laser energy source can be powered by a power supply 240 located outside of the patient's body and connected to the laser energy source 180 by a cable 250.

Figure 14:
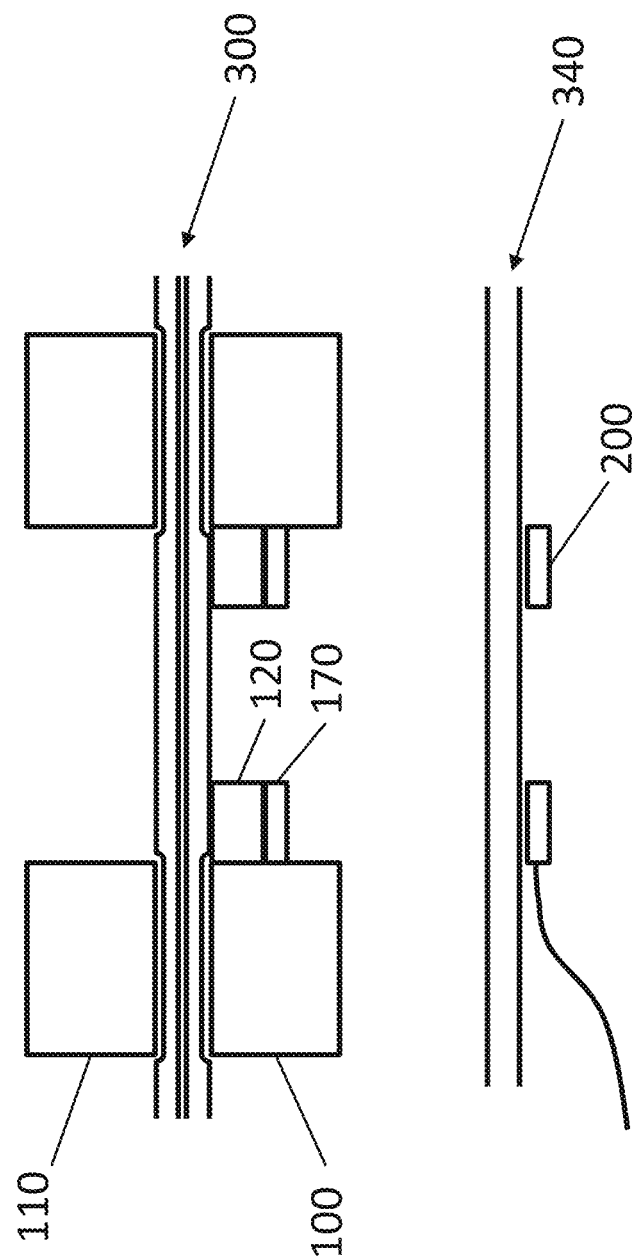
FIG. 14 is a schematic illustration of a system comprising tissue-compressing elements, a heating element and a means of wirelessly transmitting power to a heating element, in accordance with some embodiments.

Power can be delivered to a device by wireless means. FIG. 14 schematically depicts a system comprising a heating element 120 and a means of wirelessly delivering power to said heating element comprising a power transmitting means 200 and a power receiving means 170. The power transmitting means 200 can be separated from the Power can be delivered wirelessly by inductive coupling, by ultrasonic coupling, or by other means. At least one layer of tissue, such as bowel wall, can separate said power transmitting means 200 and said power receiving means 170.

Figure 15:
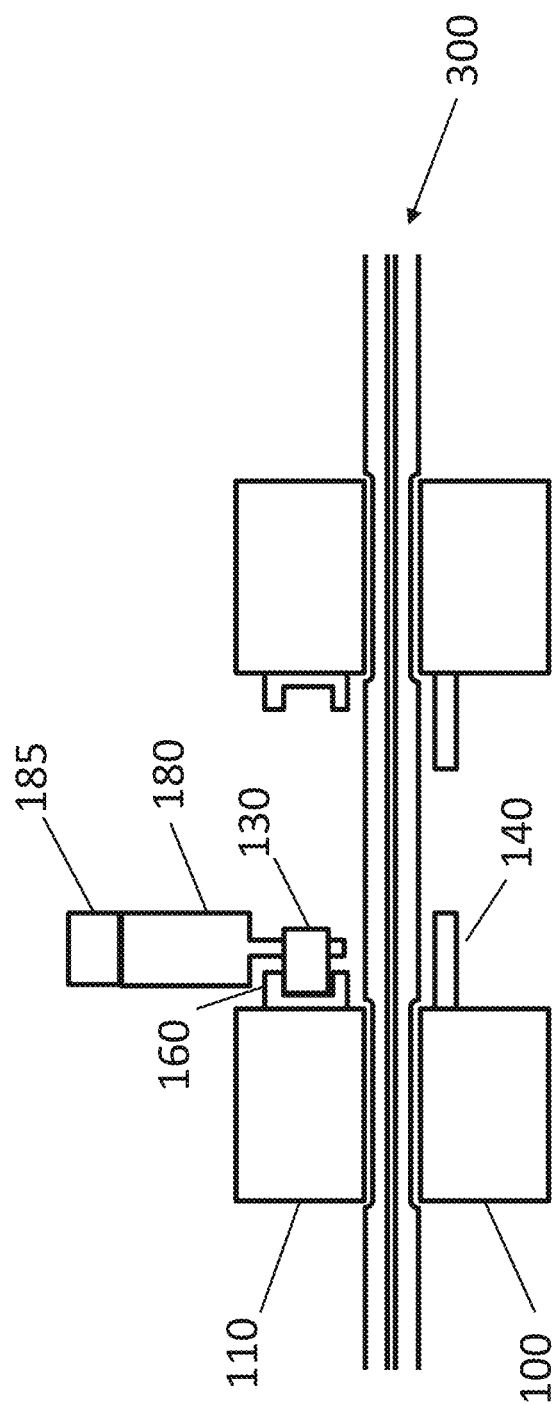
FIG. 15 is a schematic illustration of a system comprising tissue-compressing elements and a laser energy delivery means comprising a laser diode and a battery, in accordance with some embodiments.
Figure 16:
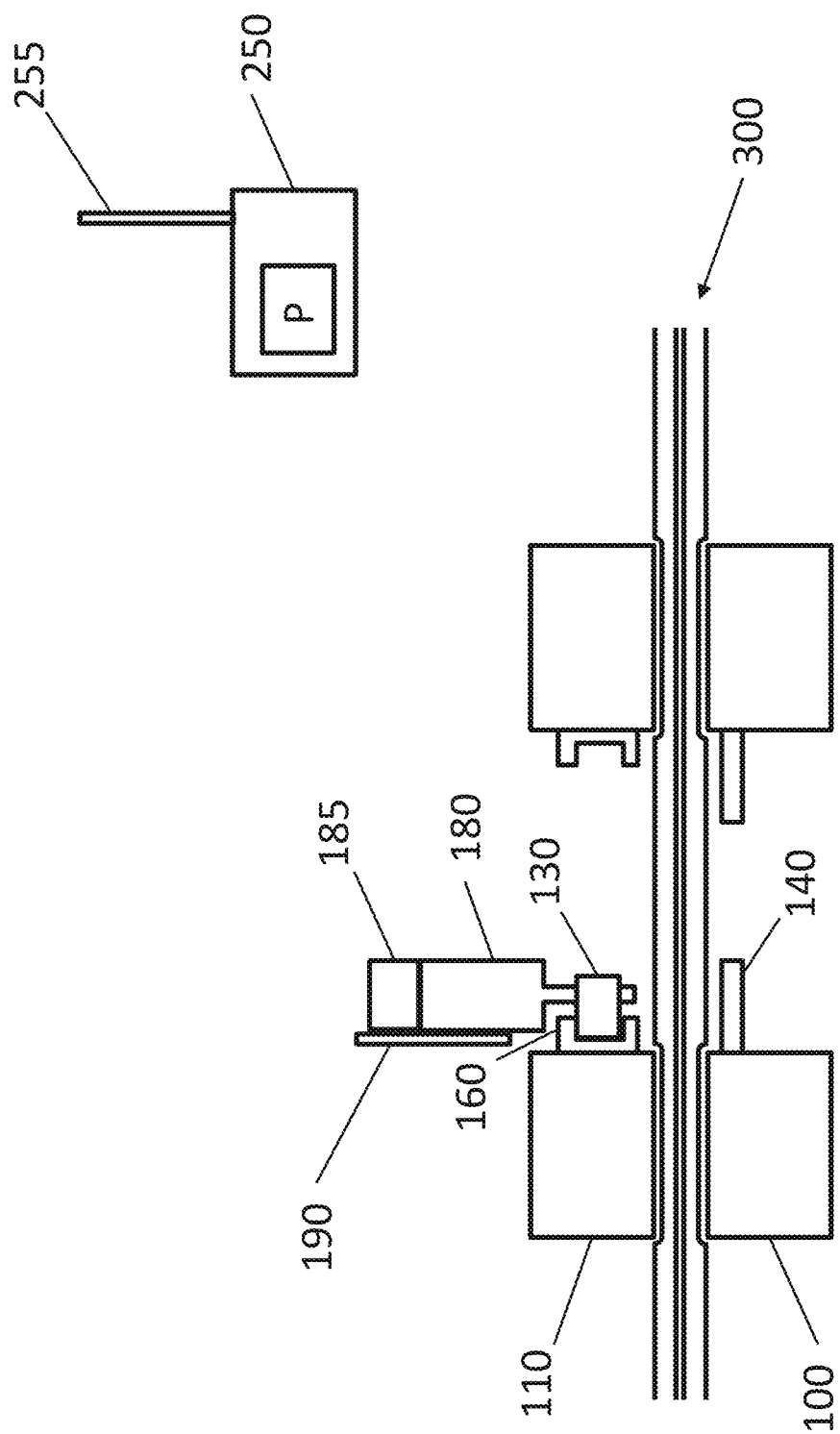
FIG. 16 is a schematic illustration of a system comprising tissue-compressing elements, a laser energy delivery means comprising a laser diode and a battery, and an external controller unit, in accordance with some embodiments.

FIG. 15 schematically depicts such a battery 185 integrated with a diode laser 180 and a tissue-compressing element 110. The battery 185 can supply power to the diode laser 180. A battery can similarly supply power to a resistive heating element. An anastomosis device that incorporates a battery 185 can operate autonomously with onboard control systems, FIG. 16 schematically depicts an anastomosis device that incorporates a battery 185 and that can operate in response to signals from a controller unit 250. An antenna 190 integrated with the anastomosis device and an antenna 255 integrated with the controller unit 250 can be used to send and receive signals.

Figure 17:
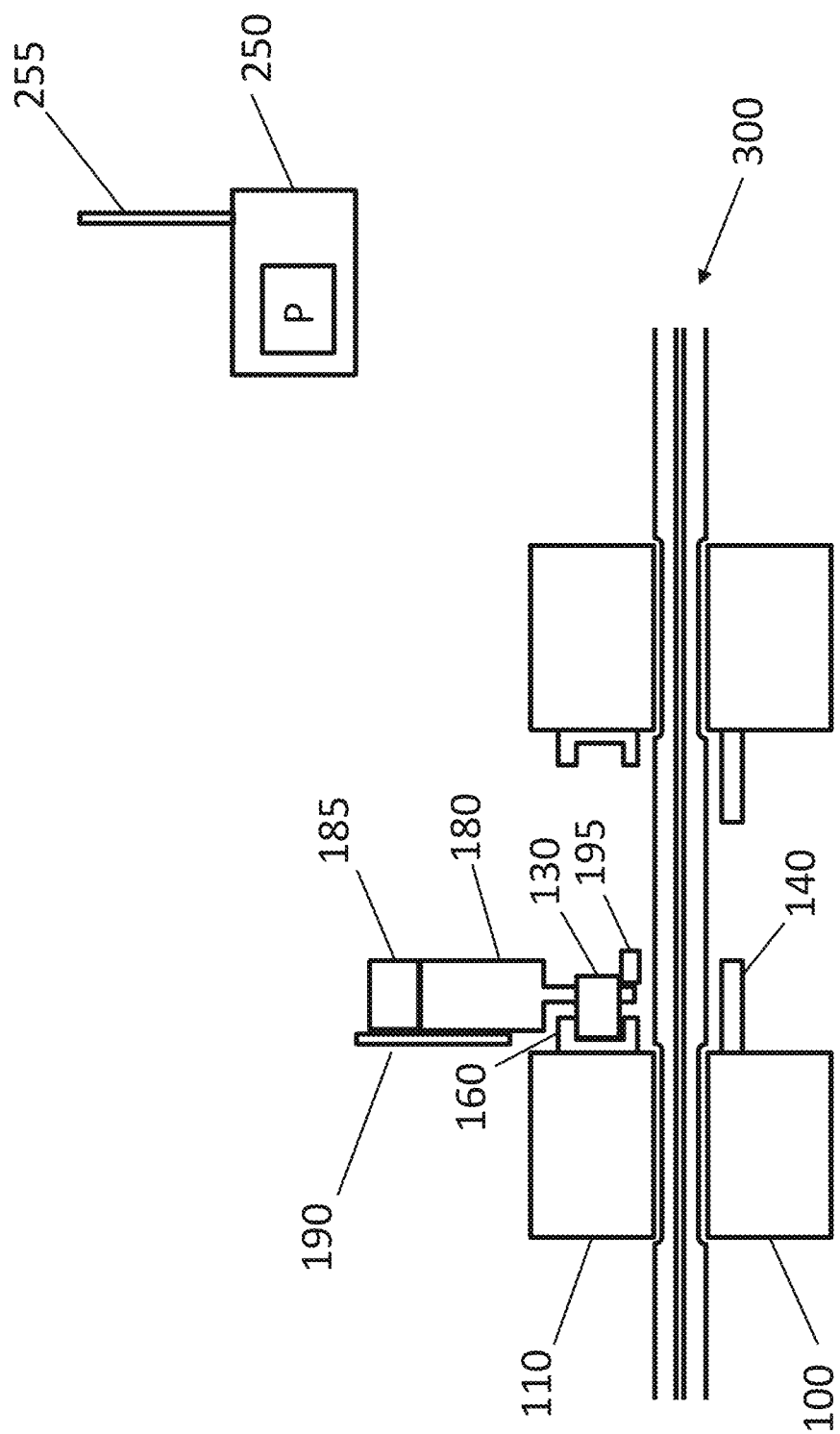
FIG. 17 is a schematic illustration of an anastomosis system with integrated sensors, in accordance with some embodiments.

FIG. 17 schematically depicts an anastomosis device that incorporates a sensing means 195 that can sense conditions of interest to a surgeon treating a patient using a device. For example, the sensing means can sense that interposed bowel wall has been cut or ablated.

Figure 18:
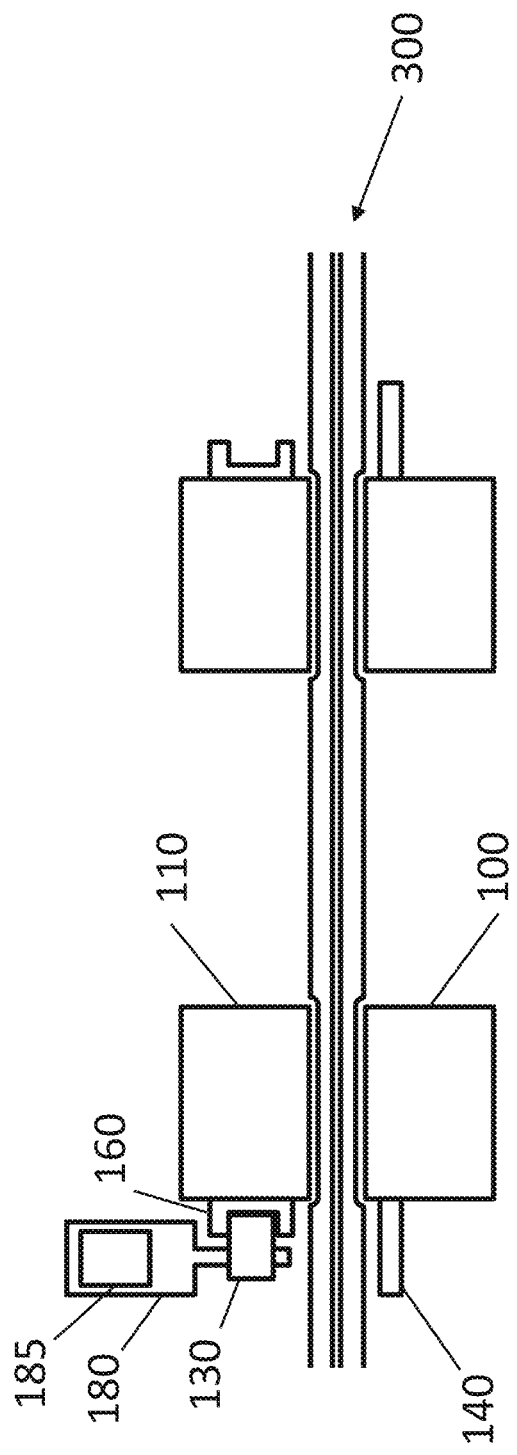
FIG. 18 is a schematic illustration of a system comprising tissue-compressing elements and a laser energy delivery means comprising a laser diode and a battery, where said laser energy delivery means is designed to deliver energy to tissue external to the interposed tissue compressed by the tissue-compressing elements, in accordance with some embodiments.

It can be beneficial for a patient to deliver laser energy to tissue peripheral to interposed tissue compressed by tissue-compressing elements. FIG. 18 schematically depicts a laser energy source integrated in an assembly with a tissue-compressing element 110, said laser energy source comprising a laser diode 180 and a battery 185 and positioned for delivery of laser energy to tissue peripheral to the tissue compressed by the tissue-compressing elements.

Figure 19:
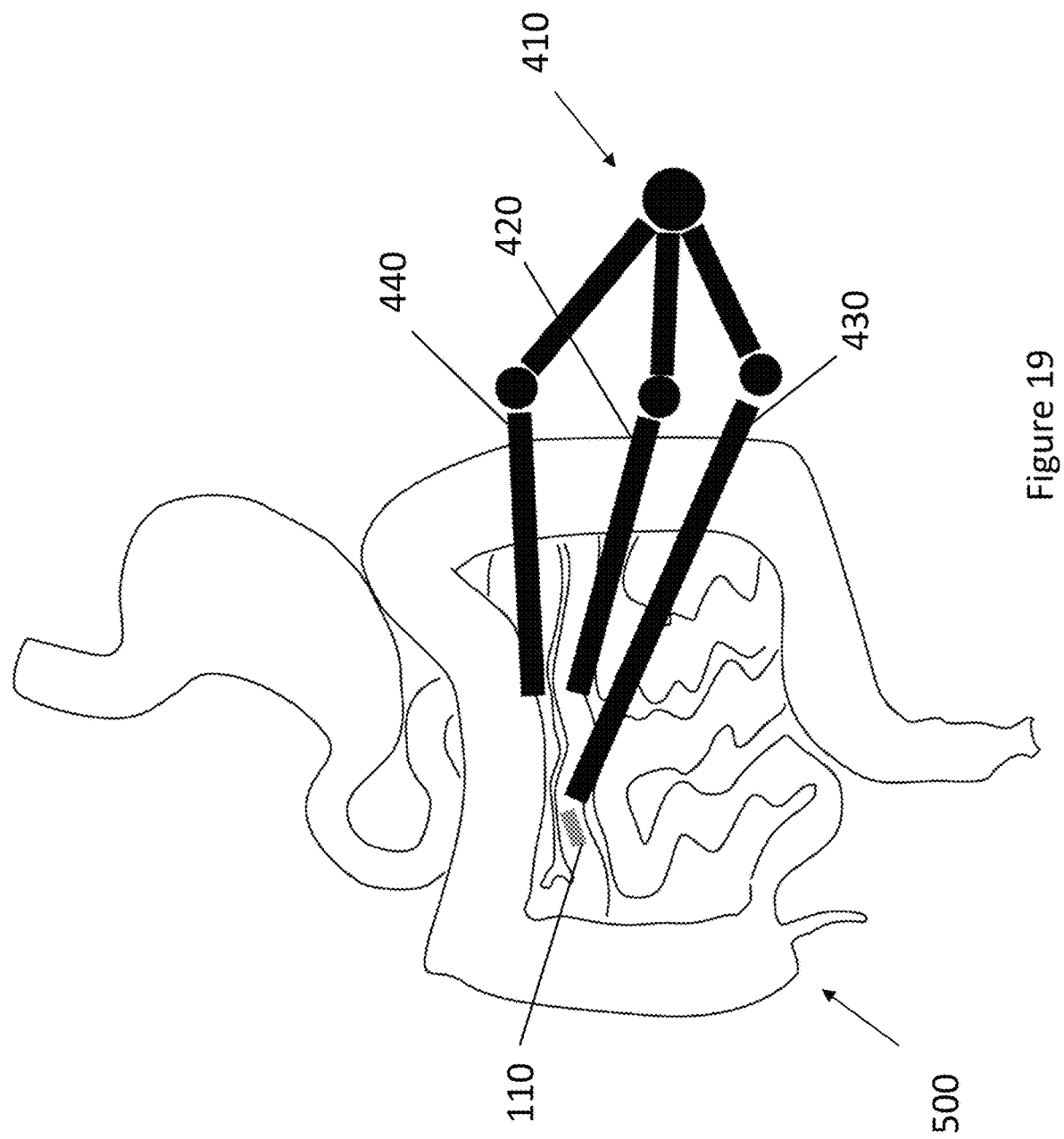
FIG. 19 is a schematic illustration of the use of a single-port robotic system with a tissue-compressing element, in accordance with some embodiments.

A variety of laparoscopic systems and tools can be used to position a tissue-compressing element in a location desired by a surgeon. FIG. 19 schematically depicts the gastrointestinal tract 500 and a single-port access surgical robotics system 410, such as the DAVINCI SP SURGICAL SYSTEM, where end effector 420 is used to constrain motion of a section of the small bowel and a second end effector 430 is used to couple through the bowel wall to a tissue-compressing element 110 in order to bring about translation of the tissue-compressing element 110 from a more proximal to a more distal position in the bowel. In some embodiments, a third end effector 440 can be used to hold a section of the colon. In some embodiments, the single port access system of the robotics system 410 comprises an endoscope, which can be provided in combination with the third end effector 430 or alternatively to the third end effector 420. The term "end effector" is known in the field of surgical robotics, and generally encompasses any structure which can be coupled to an arm of a surgical robot and manipulated to provide a desired effect on tissue.

Figure 20:
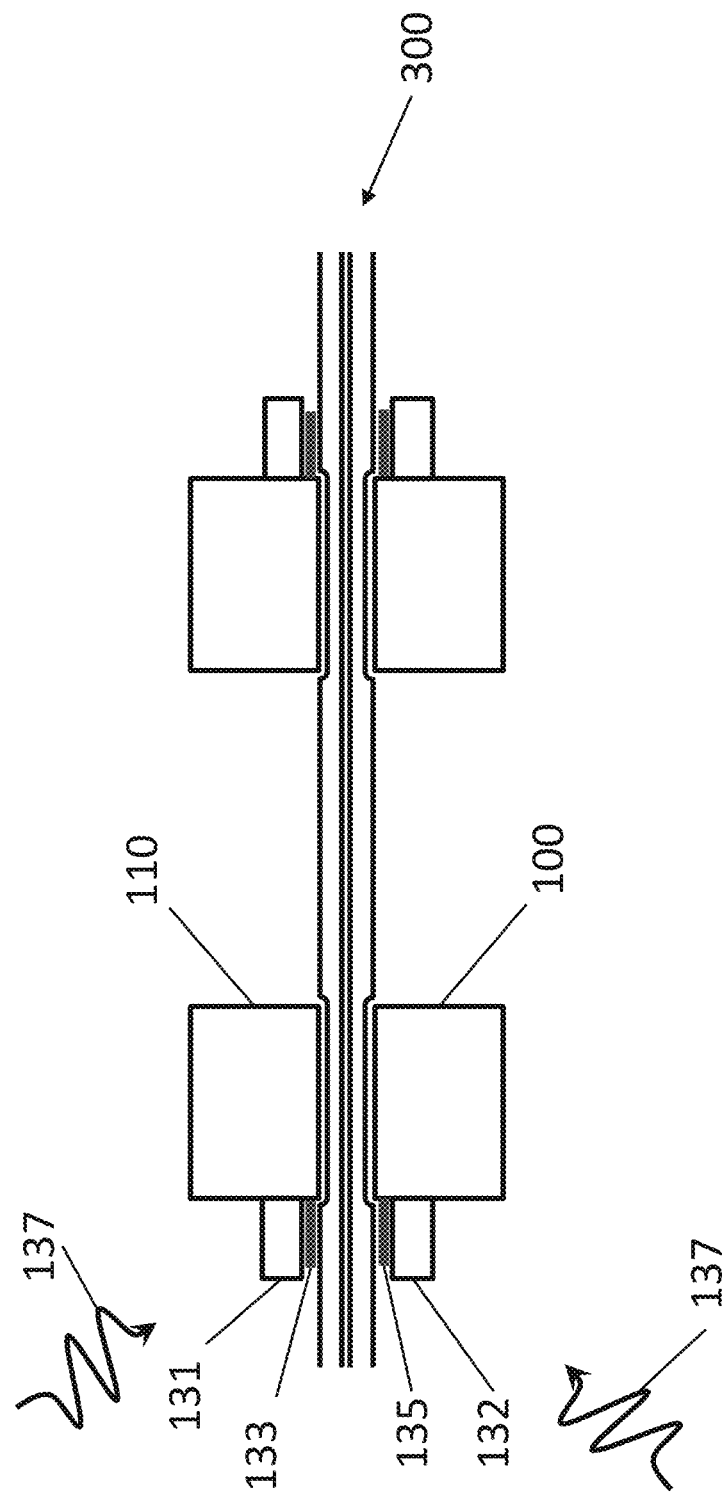
FIG. 20 is a schematic illustration of tissue-compressing elements of the intervention integrated incorporating light-activated adhesive, in accordance with some embodiments.

FIG. 20 shows a light activated adhesive used in combination with tissue-compressing elements as described herein. The tissue-compressing element 110 is coupled to an optically transmissive element 131, which allows light 137 to be transmitted to the light activated adhesive 133 through the optically transmissive element 131. In some embodiments, the tissue-compressing element comprises the optically transmissive element, and these two components may be affixed to each other prior to placement on the tissue. The optically transmissive element 131 can be sized and shaped in many ways and may comprise an approximately annular element, for example. In some embodiments, the optically transmissive element comprises a material capable of transmitting light at wavelengths at which the light-activated adhesive can be cured, such as near infrared wavelengths. The optically transmissive element 131 can combined with the tissue-compressing element 110 to form an assembly of components to form the anastomosis as described herein. In some embodiments, the optically transmissive element 131 and the tissue-compressing element 110 are approximately concentric.

The light activated adhesive can be provided in many ways. For example, a layer of adhesive 133 can be present on the surface of element 131 prior to placement. Alternatively, a quantity of adhesive can be applied to the tissue prior to placement of the optically transmissive element 131. Once the elements 110 and 131 have been placed, a sufficient quantity of light-sensitive adhesive 133 is present on or near a surface of the element 131 to promote adhesion of the optically transmissive component 131 and the tissue-compressing element 110 to the tissue. The light-activated adhesive can be activated by the light energy after the tissue-compressing element 110 has been brought into contact with tissue. Such activation can cause the assembly comprising the optically transmissive component 131 and the tissue-compressing element 110 to adhere substantially to the tissue. The element 131 can have characteristics conducive to efficiently transferring light into light-sensitive adhesive that is present on or near a surface of the element 131. For example, the element 131 can comprise materials that allow passage of a large fraction of light at a wavelength or range of wavelengths that activate the light-activated adhesive.

A second assembly may comprise tissue-compressing element 100, an optically transmissive element 132, and a second light activated adhesive 135, configured similarly to the tissue-compressing element 110, optically transmissive element 131, and adhesive 133. The second assembly can be adhered to the tissue similarly to the first component. In some embodiments, the first and second assemblies are adhered to tissue after the first and second assemblies have been coupled to each other with the tissue-compressing elements.

The adhesive, wavelengths, and optically transmissive material can be configured in many ways to promote adhesion of the elements to the tissue. In some embodiments, the light-activated adhesive comprises a chromophore to promote curing of the adhesive and adhesion of tissue-compressing elements using a light-activated adhesive. While many chromophores can be used, in some embodiments, the chromophore comprises Indocyanine green, which is a chromophore that can be used in light-activated adhesives. In some embodiments, the light-activated adhesive comprises Indocyanine green combined with chitosan. A light-activated adhesive comprising indocyanine green and chitosan can be activated using laser energy comprising infrared wavelengths. Infrared radiation can pass through many tissues with relatively little absorbance, which can allow the adhesive to be cured without substantial absorbance of the light energy transmitted through the tissue. Also, the infrared light energy can be transmitted through the tissue with decreased heating. In some embodiment, near infrared light can pass through the layers of tissue such that the adhesive on both sides of the layers can be cured with illumination from one side. For example, light can be transmitted from one side through optically transmissive element 131 to the layer of light activated adhesive 133, and also through the tissue layers of region 300 to cure the layer of light activated adhesive 135, which can facilitate curing of the adhesive during surgery.

The light can be delivered to the adhesive in many ways as described herein. In some embodiments, light is provided with a surgical instrument introduced into the patient. Alternatively or in combination, a guide such as a raceway can be used to deliver light with a laser. In some embodiments, the raceway is located on an outer surface of the tissue-compressing elements. Also, while optically transmissive elements 131, 132 are shown outside the tissue-compressing elements, in some embodiments, the optically transmissive elements are located inside the annular walls of the tissue compressive elements.

In some embodiments, the tissue facing surface of the optically transmissive element is configured to provide decreased amounts of pressure to the tissue compared to the tissue-compressing element. For example the tissue facing surface of the optically transmissive element can be located farther from the tissue than the tissue facing surface of the tissue compressive element in order to decrease pressure to the tissue from the optically transmissive structure and adhesive as compared to the tissue compressive element.

The wavelength of light to cure the adhesive may comprise any suitable wavelength. In some embodiments, the light comprises one or more wavelengths within a range from about 650 nm to about 900 nm, from about 750 nm to about 850 nm, or from about 790 nm to about 840 nm, for example.

The power of the light source directed to the tissue may comprise any suitable power. In some embodiments, the light source comprises a power within a range from about 5 mW to 500 mW, from 50 mW to about 300 mW, or from about 150 mW to 250 mW, for example.

While reference is made to indocyanine green as a chromophore and chitosan as an adhesive, one of ordinary skill in the art will recognize many adaptations and variations.

Turning back to FIG. 2, the laser light source can be a visible or infrared laser unit, such as a green light laser unit, where an optical fiber is used to direct laser energy onto regions of intervening tissue. As referred to herein, "laser fiber" refers to any of a variety of conduits that allow for passage of light energy. Laser fibers generally comprise materials that can pass laser energy with comparatively low losses. Laser fibers are coupled to laser units using optical couplers. An optional lens can be used with a laser fiber. Operation of a laser with a fiber is associated with the generation of heat. In the system shown in FIG. 2, the race and the first tissue-compressing element can sink heat from the laser.

In some embodiments a laser diode can be used in place of a laser fiber and laser unit. Some laser diode measure only a few millimeters in size, facilitating their use in a magnamosis system like that illustrated in FIG. 2. A sufficiently compact laser diode can be positioned directly in the holder 130. A power supply and controlling means can be integrated with the laser diode.

Ultrashort pulse lasers can be used to cut tissue in a manner that is favorable from the standpoint of the patient outcome or the user experience, such as carefully controlled depth and minimal production of smoke. Hollow core microstructured fibers can deliver laser energy from an ultrashort pulse laser unit located outside of the body.

A motorized mechanism can translate the laser energy delivery means to deliver laser energy to a tissue region. A stepper motor can rotate a laser fiber holder with a laser fiber along an approximately circular pathway.

In some embodiments, laser light from a source 150 can be used to enhance the positional stability of the magnamosis system without translating the laser light. Application of light energy to a region of multilayer tissue can confer stabilization through the physiological effects described above.

As a specific example, in some embodiments in which an anastomosis is to be created between the stomach and small bowel of a patient, a first tissue-compressing element can be endoscopically positioned in the stomach of the patient and a second tissue-compressing element can be placed in the small bowel of the patient. The second tissue-compressing element can be placed by upper endoscopy, with an endoscope used to transport the element past the pylorus. As yet another alternative, the second tissue-compressing element can be placed by lower endoscopy. Alternatively, the second tissue-compressing element can be laparoscopically positioned by means of an enterotomy. In some patients, a tool can be used to laparoscopically milk the second tissue-compressing element to a position within the small bowel determined by the surgeon to be favorable from the standpoint of achieving intended therapeutic outcomes. A robotic apparatus as described herein can be used to perform said milking. For endoscopic placement of the second tissue-compressing element, the endoscope used can have features and functionality associated with surgical robotics, such as systems of sensors and actuators designed to facilitate navigating the bowel. The two tissue-compressing elements can be mated using endoscopic manipulation, laparoscopic manipulation, a combination of endoscopic and laparoscopic manipulation, or by direct manipulation in an open surgery. Once mated, the laser energy source can be used to confer enhanced positional stability as described herein. The laser energy source can be used to perform additional components of a procedure such as ablating tissue.

As another example, after lower anterior resection, a first tissue-compressing element can be positioned distal to the resection and a second tissue-compressing element can be positioned proximal to the resection, and the tissue-compressing elements mated. An opening in the central tissue region can be created using energy. A suturing or stapling means can be introduced through the opening and sutures or staples can be placed around the periphery of the anastomosis. A laser energy source positioned external to a tissue-compressing means can then be translated along a circular path to cut out the tissue interposed between the tissue-compressing elements, while leaving the sutures or staples intact. This cutting action can also bring about cauterization. For an anastomosis after lower anterior resection, tissue-compressing elements having an outer diameter between 18 mm and 35 mm can be preferred.

As another example, to create a partial diversion between two sections of the small bowel, a first tissue-compressing element and a second tissue-compressing element can each be placed by upper endoscopy, with an endoscope used to transport the element past the pylorus. As yet another alternative, a first tissue-compressing element can be placed by upper endoscopy and a second tissue-compressing element placed by lower endoscopy. A first or second tissue-compressing element, or both tissue-compressing elements, can be laparoscopically positioned by means of an enterotomy. In some patients, a tool can be used to laparoscopically milk a first or second tissue-compressing element, or both elements, to a position or positions within the small bowel determined by the surgeon to be favorable from the standpoint of achieving intended therapeutic outcomes. A robotic apparatus can be used to perform said milking. For endoscopic placement of the second tissue-compressing element, the endoscope used can have features and functionality associated with surgical robotics, such as systems of sensors and actuators designed to facilitate navigating the bowel. The two tissue-compressing elements can be mated using endoscopic manipulation, laparoscopic manipulation, a combination of endoscopic and laparoscopic manipulation, or by direct manipulation in an open surgery. Once mated, the laser energy source can be used to confer enhanced positional stability as described herein. The laser energy source can be used to perform additional components of a procedure such as ablating tissue. For an anastomosis in partial diversion, tissue-compressing elements having an outer diameter between 10 mm and 18 mm can be preferred.

As another example, in treating esophageal atresia, a first tissue-compressing element can be positioned in the proximal pouch and a second tissue-compressing element can be positioned via a gastric tube in the distal pouch. For an anastomosis to treat esophageal atresia, tissue-compressing elements having an outer diameter between 4 mm and 10 mm can be preferred.

In some embodiments, the anastomosis system can comprise sensing means that can be used with the laser source to characterize the position of the tissue-compressing elements relative to one another. For example, an optical sensor system operating at a wavelength which is passed by tissue can sense the relative position of two tissue-compressing elements. For example, the sensing system can provide information about distances separating two tissue contacting faces, including misalignment. Tissue contacting faces that are further apart than a threshold separation distance may reflect interposing tissue features such as scarring that can be associated with poor outcomes. A sensing means can also comprise a temperature sensing means that can provide information as to whether tissue temperatures are within a desired range. Sensing means can indicate and communicate sensing information by any of a wide range of indicating and communicating means.

While approximately annular magnetic elements have advantages from the standpoint of self-alignment, we note that tissue-compressing elements can have a variety of shapes.

A laser energy source can be connected to a laser energy delivery means by a fiber and the laser energy delivery means can be used to delivery laser energy to tissue to bring about a desired degree of injury to stabilize a magnamosis device and/or to bring about immediate patency.

A variety of endoscopic, laparoscopic, and hybrid endoscopic-laparoscopic techniques can be employed in achieving desirable outcomes in patients using systems and devices. Tissue-compressing devices can be positioned in the small bowel using an endoscope and then translated distally in the small bowel by manipulating the tissue-compressing device within the bowel. In an open procedure, a surgeon can manually translate a tissue-compressing device distally within the bowel by grasping or otherwise constraining the motion of the region of the bowel immediately proximal to the device with one hand and using two fingers of the other hand to apply force to the device through the bowel wall. In a laparoscopic procedure, pincer-like laparoscopic tools can be used to replicate such manual milking of the tissue-compressing device through the bowel. In a robotic-assisted laparoscopic procedure, a first arm and a second arm can be used to milk a tissue-compressing device distally within the small bowel. After a first device has been milked distally, a second device can be similarly milked distally, to a position in the small bowel proximal to the position to which said first device was milked. Said first and second devices can then be mated with two layers of small bowel wall interposed between the tissue-contacting faces of said first and second devices. Energy can be applied to enhance anastomosis formation. For example, current can be passed through resistive heating elements to heat interposed regions of bowel wall. As another example, laser energy can be applied to interposed regions of bowel wall. The laser energy source can be used to apply laser energy to a region of bowel that is centrally positioned relative to the tissue-compressing components. Such application of laser energy to a centrally located region can bring about immediate patency. Such application of laser energy to a centrally located region can bring about swelling that tends to maintain the positional stability of the mated devices. A laser energy source can be translated through an approximately circular path. Translating a laser energy source on a circular path can cleanly cut a hole in interposed bowel wall. For a circular path with a radius smaller than the inside radius of mated annular tissue-compressing devices, translating a laser source can cut a hole to achieve immediate patency. For a circular path with a radius larger than the outside radius of mated annular tissue-compressing devices, translating a laser source can thermally weld a region of bowel wall. Translating a laser energy source in this manner can also cut.

For robotic laparoscopic procedures, a third arm can lift away a portion of the large bowel to facilitate milking and mating.

Access into the abdomen for said first, second and third arms can be through multiple ports or through a single port.

Power for the operation of a resistive heater or a laser energy source can be supplied via a tether. For an anastomosis device that is intended to bring about anastomosis over a period of several days, a fuse can be used to detach the tether from the anastomosis device, after which the tether can be removed. Power for a resistive heater or laser energy source can be supplied wirelessly. Power can be wirelessly supplied inductively. Power can be wirelessly supplied by ultrasound. An inductive or ultrasonic means for wirelessly supplying power can be introduced and positioned laparoscopically, using conventional laparoscopic instrumentation or using a surgical robot.

EXPERIMENTAL

Figure 21B:
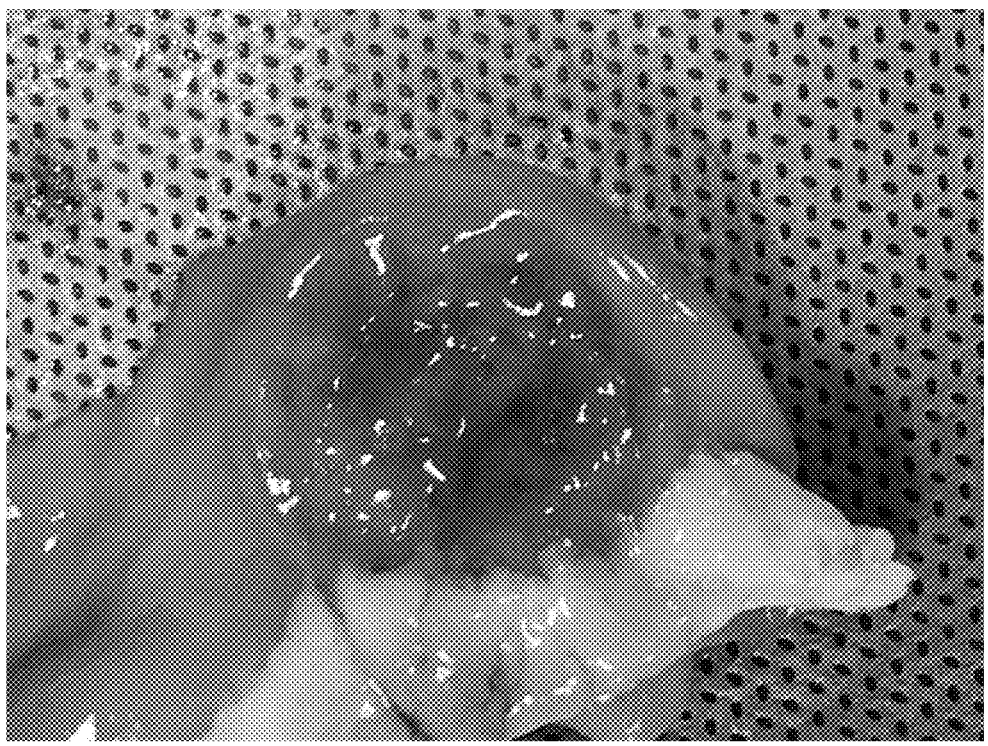
FIGS. 21A and 21B show tissue adhered to tissue-contacting elements with a light activated adhesive, in accordance with embodiments of the present disclosure.
Figure 21A:

The present inventors have conducted experiments in accordance with the present disclosure. FIGS. 21A and 21B illustrate the use of a light-activated adhesive comprising indocyanine green and chitosan in combination with a tissue-compressing element, with the light-activated adhesive activated by a 200 mW 808 nm laser. FIG. 21A shows a magnetic element as described herein adhered to a section of tissue, in which the element adheres sufficiently for the adhesive to support the weight of the tissue-compressing element. FIG. 21B shows the back side of the tissue adhered to the tissue-compressing element of FIG. 21A, in which good connection between the tissue and the tissue-compressing element is shown.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. In some embodiments, the term "about" encompasses +/−30% or +/−20% or +/−10% or +/−5% or +/−less than 5%.

The present disclosure includes the following numbered clauses.

Clause 1. A system for forming an anastomosis between a first layer of tissue and a second layer of tissue of a patient's body, the system comprising: a plurality of magnetic elements configured to couple to each other with the first layer of tissue and the second layer of tissue between the plurality of magnetic elements; and a guide coupled to an energy source, the guide configured to move the energy source in relation to the plurality of magnetic elements to resect the first tissue layer and the second tissue layer in order to provide the anastomosis.

Clause 2. The anastomosis system of clause 1, wherein the energy source is configured to emit one or more of laser energy or electrocautery energy.

Clause 3. The anastomosis system of clause 1, wherein the energy source comprises one or more electrodes configured to emit to electrocautery energy.

Clause 4. The anastomosis system of clause 1, wherein the energy source is configured to emit laser energy to form the anastomosis.

Clause 5. The anastomosis system of clause 4, wherein a laser is coupled to the energy source, the laser comprising one or more of a diode laser, a gas laser, a solid state laser, a continuous laser, a pulsed laser, a picosecond laser, or a femtosecond laser and optionally wherein the laser source is configured to emit an average power within a range from 1 Watt to 10 Watts.

Clause 6. The anastomosis system of clause 4, wherein the energy source is configured to deliver laser energy from a laser located outside the patient's body with an optical fiber coupled to the guide to deliver the laser energy, the laser energy comprising one or more of ultraviolet light, visible light, infrared light, near infrared light or far infrared light.

Clause 7. The anastomosis system of clause 6, wherein said laser comprises a carbon monoxide laser configured to emit laser energy comprising a wavelength within a range from 4 to 6 micro-meters (microns).

Clause 8. The anastomosis system of clause 4, wherein the energy source is configured to emit energy from a diode laser and optionally wherein said diode laser is configured for insertion into the patient.

Clause 9. The anastomosis system of clause 8, wherein said diode laser comprises a gallium nitride laser emitting laser energy comprising a wavelength within a range from 360 to 480 nm.

Clause 10. The anastomosis system of clause 1, wherein the guide is configured to move the energy source in relation to the plurality of magnetic elements in order to provide the anastomosis.

Clause 11. The anastomosis system of clause 10, wherein the guide comprises a track configured to move the energy source along a path around a central location defined by the plurality magnetic elements and wherein the path comprises a substantially closed path in order to allow resected tissue from the first layer and the second layer to separate from the first layer and the second layer, respectively, to form the anastomosis.

Clause 12. The anastomosis system of clause 10, wherein the plurality of magnetic elements is arranged to define a substantially annular region wherein the guide is configured to move the energy source in relation to the substantially annular region in order to form the anastomosis.

Clause 13. The anastomosis system of clause 12, wherein the guide is configured to move the energy source approximately concentric to a substantially annular region.

Clause 14. The anastomosis system of clause 10, wherein the guide is configured to move the energy source along an interior of the substantially annular region.

Clause 15. The anastomosis system of clause 10, where the guide comprises an approximately annular track to move the energy source along a path and optionally wherein the path comprises an approximately circular path.

Clause 16. The anastomosis system of clause 1, further comprising an actuator coupled to the guide to move the energy source with the guide along a path, and optionally wherein the actuator comprises one or more of a spring, a motor, a stepper motor, a servo motor, a piezoelectric actuator, a coil, or an extension coupled to an external handpiece.

Clause 17. The anastomosis system of clause 1, further comprising a sensor.

Clause 18. The anastomosis system of clause 17, where said sensor is configured to sense a position of the plurality of magnetic elements relative to each other.

Clause 19. The anastomosis system of clause 17, where said sensor is configured to measure laser energy from a laser energy source.

Clause 20. The anastomosis system of clause 17, wherein said sensor is configured to measure a temperature.

Clause 21. The anastomosis system of clause 17, wherein said sensor is configured to measure an intensity of energy to the sensor as an indicator of a presence or an absence of intervening tissue layers located between the plurality of magnetic elements in response to the intensity of energy to the sensor.

Clause 22. The anastomosis system of clause 1, further comprising a stop to absorb light energy from a laser energy source, the stop located on an opposite side of the plurality of tissue layers from the energy source.

Clause 23. The anastomosis system of clause 19, wherein the stop comprises an approximately annular structure positioned interior or exterior to one or more of the plurality of magnetic elements and comprising a material to absorb light energy.

Clause 24. The anastomosis system of clause 1, wherein the plurality of magnetic elements comprises a first magnet comprising a first face and a second magnet comprising a second face to engage the first face through the plurality of tissue layers, said first face comprising a convex surface with a first radius of curvature, said second face comprising a concave surface with a second radius of curvature and wherein said second radius of curvature is greater than said first radius of curvature.

Clause 25. The anastomosis system of clause 1, wherein each of said plurality of magnetic elements comprises an outer diameter within a range from 18 mm to 35 mm.

Clause 26. The anastomosis system of clause 1, wherein each of said plurality of magnetic elements comprises an outer diameter within a range from 10 mm to 18 mm.

Clause 27. The anastomosis system of clause 1, wherein each of said plurality of magnetic elements comprises an outer diameter within a range from 4 mm to 10 mm.

Clause 28. The anastomosis system of clause 1, wherein each of said plurality of magnetic elements comprises a plurality of engagement structures configured to engage a corresponding plurality of engagement structures on a corresponding magnet.

Clause 29. The anastomosis system of clause 28, wherein the plurality of engagement structures comprises a plurality of protrusions and a plurality of recesses shaped to receive the plurality of protrusions.

Clause 30. The anastomosis system of clause 29, wherein the plurality of protrusions comprises a plurality of convex surfaces and the plurality of recesses comprises a plurality of concave surfaces.

Clause 31. The anastomosis system of clause 29, wherein the plurality of protrusions comprises at least three protrusions and the plurality of recesses comprises at least three recesses.

Clause 32. The anastomosis system of clause 1, further comprising a coil operatively coupled to the energy source to power the energy source.

Clause 33. A system for forming an anastomosis between a first layer of tissue and a second layer of tissue of a patient's body, the system comprising: a plurality of magnetic elements configured to couple to each other between the first layer of tissue and the second layer of tissue; and an activatable adhesive configured to couple to one or more of the plurality of magnetic elements to one or more of the first layer of tissue or the second layer of tissue.

Clause 34. The system of clause 33, wherein the activatable adhesive comprises one or more of thermally activatable adhesive, a chemically activatable adhesive, or a light activatable adhesive.

Clause 35. The system of clause 33, further comprising an energy source to activate the activatable adhesive with one or more of heat or light.

Clause 36. The system of clause 35, wherein the energy source comprises an electrical heating element.

Clause 37. The system of clause 33, wherein the thermally activated adhesive is located one or more tissue engaging surfaces of the plurality of magnetic elements prior to thermally activating the adhesive.

Clause 38. A method of treating tissue, the method comprising: advancing a first magnetic element into a patient; and manipulating the magnetic element through an intestinal wall with a first robotic end effector to position the magnetic element; and coupling the first magnetic element to the second magnetic element with a second robotic end effector to form an anastomosis.

Clause 39. The system or method of anyone of the preceding clauses wherein each of the plurality of magnetic elements comprises an exposed magnetic material.

Clause 40. The system or method of anyone of the preceding clauses wherein each of the plurality of magnetic elements comprises a magnetic material and a coating.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A system for forming an anastomosis between a first layer of tissue and a second layer of tissue of a patient's body, the system comprising: a plurality of magnetic elements configured to couple to each other with the first layer of tissue and the second layer of tissue between the plurality of magnetic elements, each of the plurality of magnetic elements having an inner curved surface; an energy source; and a guide coupled to the energy source, the guide configured to move the energy source in relation to the plurality of magnetic elements to resect the first tissue layer and the second tissue layer in order to provide the anastomosis; wherein the guide comprises a raceway coupled to the energy source, the raceway located on the inner curved surface of one of the plurality of magnetic elements to move the energy source relative to the raceway along a path around a central location defined by the plurality of magnetic elements.

2. The anastomosis system of claim 1, wherein the energy source is configured to emit one or more of laser energy or electrocautery energy.

3. The anastomosis system of claim 1, wherein the energy source comprises one or more electrodes configured to emit electrocautery energy.

4. The anastomosis system of claim 1, wherein the energy source is configured to emit laser energy to form the anastomosis.

5. The anastomosis system of claim 4, wherein a laser is coupled to the energy source, the laser comprising one or more of a diode laser, a gas laser, a solid state laser, a continuous laser, a pulsed laser, a picosecond laser, or a femtosecond laser.

6. The anastomosis system of claim 4, wherein the energy source is configured to deliver laser energy from a laser located outside the patient's body with an optical fiber coupled to the guide to deliver the laser energy, the laser energy comprising one or more of ultraviolet light, visible light, infrared light, near infrared light or far infrared light.

7. The anastomosis system of claim 6, wherein said laser comprises a carbon monoxide laser configured to emit laser energy comprising a wavelength within a range from 4 to 6 micro-meters (microns).

8. The anastomosis system of claim 4, wherein the energy source is configured to emit energy from a diode laser.

9. The anastomosis system of claim 8, wherein said diode laser comprises a gallium nitride laser emitting laser energy comprising a wavelength within a range from 360 to 480 nm.

10. The anastomosis system of claim 1, wherein the path comprises a substantially closed path in order to allow resected tissue from the first layer and the second layer to separate from the first layer and the second layer, respectively, to form the anastomosis.

11. The anastomosis system of claim 1, wherein the plurality of magnetic elements is arranged to define a substantially annular region wherein the guide is configured to move the energy source in relation to the substantially annular region in order to form the anastomosis.

12. The anastomosis system of claim 11, wherein the guide is configured to move the energy source approximately concentric to the substantially annular region.

13. The anastomosis system of claim 11, wherein the guide is configured to move the energy source along an interior of the substantially annular region.

14. The anastomosis system of claim 1, where the raceway comprises an approximately annular track to move the energy source along the path.

15. The anastomosis system of claim 1, further comprising an actuator coupled to the guide to move the energy source with the guide along the path.

16. The anastomosis system of claim 1, further comprising a sensor.

17. The anastomosis system of claim 16, where said sensor is configured to sense a position of the plurality of magnetic elements relative to each other.

18. The anastomosis system of claim 16, wherein said sensor is configured to measure energy from the energy source.

19. The anastomosis system of claim 16, wherein said sensor is configured to measure a temperature.

\* \* \* \* \*